United States Patent
Sverdlove et al.

(10) Patent No.: US 10,973,749 B2
(45) Date of Patent: Apr. 13, 2021

(54) COSMETIC COMPOSITION COMPRISING VITAMIN C AND CERAMIDES

(71) Applicant: L'OREAL, Paris (FR)

(72) Inventors: Madeline Jane Sverdlove, Jersey City, NJ (US); Patricia Brieva, Manalapan, NJ (US); Maggie Su, Cranford, NJ (US); Andrew B. Goldberg, Springfield, NJ (US); Wendy Corrine Pagan, Garfield, NJ (US)

(73) Assignee: L'OREAL, Paris (FR)

( * ) Notice: Subject to any disclaimer, the term of this patent is extended or adjusted under 35 U.S.C. 154(b) by 3 days.

(21) Appl. No.: 16/369,168

(22) Filed: Mar. 29, 2019

(65) Prior Publication Data

US 2020/0306165 A1 Oct. 1, 2020

(51) Int. Cl.

| A61K 8/67 | (2006.01) |
|---|---|
| A61K 8/44 | (2006.01) |
| A61K 8/34 | (2006.01) |
| A61K 8/41 | (2006.01) |
| A61K 8/36 | (2006.01) |
| A61K 8/37 | (2006.01) |
| A61K 8/46 | (2006.01) |
| A61K 8/68 | (2006.01) |

(52) U.S. Cl.
CPC ............... *A61K 8/676* (2013.01); *A61K 8/34* (2013.01); *A61K 8/342* (2013.01); *A61K 8/345* (2013.01); *A61K 8/36* (2013.01); *A61K 8/37* (2013.01); *A61K 8/416* (2013.01); *A61K 8/44* (2013.01); *A61K 8/466* (2013.01); *A61K 8/68* (2013.01); *A61K 2800/48* (2013.01); *A61K 2800/87* (2013.01)

(58) Field of Classification Search
CPC .......... A61K 8/676; A61K 8/68; A61K 8/416; A61K 8/345; A61K 8/34; A61K 8/37; A61K 8/466; A61K 8/44; A61K 8/36; A61K 8/342; A61K 2800/48; A61K 2800/87
See application file for complete search history.

(56) References Cited

U.S. PATENT DOCUMENTS

| 2002/0197289 | A1 | 12/2002 | Chevalier et al. |
|---|---|---|---|
| 2003/0190338 | A1 | 10/2003 | Castiel et al. |
| 2003/0224077 | A1 | 12/2003 | Mahe et al. |
| 2004/0248294 | A1 | 12/2004 | Chopart et al. |
| 2007/0148771 | A1 | 6/2007 | Chopart et al. |
| 2008/0213323 | A1 | 9/2008 | De Lacharriere et al. |
| 2010/0291007 | A1 | 11/2010 | Mahe et al. |
| 2011/0319486 | A1 | 12/2011 | Vivier et al. |
| 2017/0112736 | A1* | 4/2017 | Meyer .............. A61Q 19/00 |
| 2017/0189297 | A1* | 7/2017 | De Lemos ........ A61Q 19/00 |

FOREIGN PATENT DOCUMENTS

WO 2017116950 A1 7/2017

OTHER PUBLICATIONS

La Roche-Posay Active C10 https://dermwarehouse.com/product/la-roche-posay-active-c10-1-oz/?keyword=&gclid=EAIaIQobChMl1qrAjten4QIVg1mGCh0fxw3AEAAYBCAAEgLvv_D_BwE.
Phloretin CF https://www.dermstore.com/product_Phloretin+CF_20342.htm?gclid=EAIaIQobChMI-_-25den4QIVSgOGCh0XqA_PEAAYAiAAEgLzgfD_BwE&utm_source=google&utm_medium=paid_search&utm_term=phloretin+cf&utm_campaign=100113.

* cited by examiner

*Primary Examiner* — Robert S Cabral
(74) *Attorney, Agent, or Firm* — Polsinelli PC

(57) ABSTRACT

The present disclosure relates to stable cosmetic compositions for delivering high amounts of ascorbic acid (vitamin C) and ceramides to the skin, products containing such cosmetic compositions, and methods for treating skin using the cosmetic compositions. The cosmetic compositions include ascorbic acid, one or more ceramides, panthenol, one or more monoalcohols having from 2 to 6 carbon atoms, one or more polyols, one or more fatty compounds, one or more emulsifiers, one or more cationic surfactants, and water. The cosmetic compositions are particularly useful for treating the effects of skin aging, for example, reducing the appearance of wrinkles and improving skin tone.

19 Claims, No Drawings

COSMETIC COMPOSITION COMPRISING VITAMIN C AND CERAMIDES

FIELD OF THE INVENTION

The present disclosure relates to cosmetic compositions comprising high amounts of ascorbic acid (vitamin C) and ceramides, products containing the cosmetic compositions, and methods for treating skin using the cosmetic compositions.

BACKGROUND OF THE INVENTION

Skin acts as a natural barrier between internal and external environments and therefore plays an important role in vital biological functions such as protection against mechanical and chemical injury, micro-organisms, and ultraviolet damage. Human skin is made up mainly of two main layers, the dermis and the epidermis, which superficially covers the dermis. The dermis provides the epidermis with a solid support. The dermis is composed mainly of fibroblasts and an extracellular matrix of collagen, elastin, and a substance known as ground substance. These components are synthesized by the fibroblasts.

The epidermis, which covers the dermis and is in direct contact with the external environment, has the main role of protecting the body against the dehydration and external attack. Natural human epidermis is composed mainly of three types of cells, namely keratinocytes, which form the vast majority, melanocytes and Langerhans cells. Each of these cell types contributes to protecting the body against external attacking factors (the weather, ultraviolet rays, tobacco, etc.). The epidermis is a keratinized, stratified pavement of epithelium that is about 90% keratinocytes. The gradual differentiation of the cells of the basal membrane, which separates the dermis from the epidermis, towards the surface of the epidermis includes the differentiation of keratinocytes, which migrate towards the surface of the skin, where they desquamate.

Ageing of the epidermis results in a reduction of thickness. Atrophy of the epidermis is the consequence of the slowing down of keratinocyte proliferation and of the accumulation of senescent keratinocytes. The outer layer becomes dull. The cells constituting the epidermis are delimited by a lipid domain. In the course of differentiation, phospholipids, the role of which consists in producing the fluid structure of the cell membranes of the living layers of the epidermis, are gradually replaced by a mixture composed predominantly of fatty acids, cholesterol and ceramides (sphingolipids).

These lipids are organized in specific lamellar structures, the integrity of which depends on the quality of the fractions present, but also on their respective proportions. This lamellar structure of the lipids of the lipid domain of the epidermis is responsible for the fluidity and thus the suppleness of the skin. The lipids are also responsible for the "barrier" properties of the epidermis, particularly of the stratum corneum.

The epidermal lipids are mainly synthesized in living epidermis. They are made up mainly of phospholipids, sphingolipids, cholesterol, free fatty is acids, triglycerides, cholesterol esters and alkanes. The phospholipids are essential for the constitution of cell membranes. They play an important role in the mediation of extracellular signals and the formation of free aliphatic chains used for energy production. They constitute a reservoir of free fatty acids necessary for the constitution of the sphingolipids. The cholesterol plays a fundamental role in moisturization of the skin and in the "barrier" function of the epidermis. Free fatty acids play a major role in maintaining the lamellar structure of the lipids of the stratum corneum, and also in the constitution of cell membranes, where they are responsible for the membrane fluidity, but also for physiological processes such as the functioning of receptors or enzymatic activity.

Ceramides are lipids that play a paramount role in the metabolism of the epidermis, and are necessary for maintaining the multilamellar structure of the intercorneocytic lipids. They are also essential for the "barrier" function of the epidermis and for water exchanges, especially for overcoming age-related moisturization problems. It has been suggested that ascorbic acid (vitamin C), and certain derivatives thereof, may promote an increase in the synthesis of ceramides.

Vitamin C is a potent antioxidant that can be used topically in dermatology to treat and prevent changes associated with photoageing, hyperpigmentation, etc. Vitamin C is very unstable and difficult to formulate and deliver into the dermis. Research has been ongoing to develop stable compositions that deliver high amounts of ascorbic acid to the skin.

SUMMARY OF THE DISCLOSURE

The present disclosure relates to cosmetic compositions that are unique in comparison to conventional cosmetic compositions because they contain and deliver a high concentration of ascorbic acid and ceramides to the skin. Ascorbic acid and ceramides are both very difficult to stabilize, each for different reasons, and therefore pose unique formulations challenges. Product have been developed that individually contain and deliver ascorbic acid and individually contain and deliver ceramides, but technology allowing for both to be formulated together, especially in high amounts, has been elusive.

The inventors successfully developed cosmetic compositions that include high amounts of ascorbic acid and ceramides, which are stable, effective, and easy to use. While not wishing to be bound by any particular theory, the inventors believe that panthenol and one or mono-alcohols having from 2 to 6 carbon atoms (e.g., ethanol), in combination with other components of the compositions, contribute to the stability and effectiveness of the compositions. The cosmetic compositions typically include:
  (a) about 5 to about 15 wt. % of ascorbic acid;
  (b) one or more ceramides;
  (c) about 0.1 to about 10 wt. % of panthenol;
  (d) about 1 to about 20 wt. % of one or more monoalcohols having from 2 to 6 carbon atoms;
  (e) about 1 to about 25 wt. % of one or more polyols;
  (f) about 1 to about 25 wt. % of one or more fatty compounds;
  (g) one or more emulsifiers;
  (h) optionally, one or more cationic surfactants; and
  (i) water.

The compositions have a pleasant texture and are easily applied to the skin, into which the vitamin C and ceramides can be absorbed. The cosmetic compositions may be in the form of an emulsion, for example, an oil-in-water emulsion. The viscosity of the cosmetic composition can vary but is typically from about 5,000 cP to 50,000 cP at 25° C. Thus, the compositions may have a lotion-like consistency. In some instances, the pH of the cosmetic composition is from about 4 to less than 7. It can be useful for the pH to be acidic (less than 7) to help stabilize the ascorbic acid.

The ascorbic acid is pure L-ascorbic acid (vitamin C), and is typically present in the cosmetic composition in an amount of from about 5 wt. % to about 15 wt. %, based on the total weight of the composition. In some cases, the amount of ascorbic acid is higher than 5 wt. %, for example from about 6 wt. % to about 15 wt. %, from about 8 wt. % to about 15 wt. %, from about 9 wt. % to about 15 wt. %, or from about 10 wt. % to about 15 wt. %, based on the total weight of the composition.

Non-limiting examples of ceramides include ceramide-EOS, ceramide-NS, ceramide-NP, ceramide-EOH, ceramide-AS, ceramide-NH, ceramide-AP, ceramide-AH, Ceramide-OS, ceramide-OH, and a mixture thereof. The total amount of ceramides may vary, but is typically greater than zero to about 5 wt. %, based on the total weight of the composition.

Non-limiting examples of monoalcohols having from 2 to 6 carbon atoms include ethanol, propanol, butanol, pentanol, hexanol, isopropyl alcohol, cycohexanol, isobutyl alcohol, 2-methyl-2-butanol (2-methylbutan-2-ol), and a mixture thereof. In one embodiment, the one or more monoalcohols include ethanol.

Useful polyols include those having from 2 to 15 carbon atoms and at least two hydroxyl groups. For example, the one or more polyols may be chosen from ethylene glycol, butylene glycol, hexylene glycol, pentylene glycol, 1,3-propanediol, diethylene glycol, dipropylene glycol, caprylyl glycol, glycerin, and a mixture thereof. In another instance, the one or more polyols include glycerin.

Non-limiting examples of useful fatty compounds include those having one or more alkyl esters, for example, those chosen from fatty acid monoesters and diesters, polyol esters, polyglycerol esters, polyglycerol polyricinoleate, polyglycerol poly-12-hydroxystearate, polyglycerol dimerate isostearate, ethylhexanoate, polyglycerol esters, and a mixture thereof. In one instance, the fatty compound(s) may include one or more fatty acid monoesters.

The one or more emulsifiers may be amphoteric, anionic, cationic, or nonionic emulsifier, and used alone or as a mixture, and optionally with a co-emulsifier. The emulsifiers are chosen in an appropriate manner according to the emulsion to be obtained. In some instances, one or more of the emulsifier include one or more nonionic emulsifiers.

Non-limiting examples of cationic surfactants include quaternary ammonium compounds, for example, behentrimonium chloride, cetrimonium chloride, behetrimonium methosulfate, and a mixture thereof.

The instant disclosure also relates to cosmetic products, for example, products comprising a container and a cosmetic composition according to the instant disclosure contained therein. A unique feature of the product is that the pressure within the container when closed does not increase by 0.5 bar or more after four weeks at a temperature of 45° C.

The cosmetic compositions are useful for treating skin, for example, the skin of the face and neck of a human. Thus, the instant disclosure relates to methods of treating the skin comprising application of the cosmetic composition of the instant disclosure to the skin. The cosmetic compositions are additionally useful in methods for treating skin dryness, repairing skin damage due to photoaging, and diminishing the appearance of wrinkles, dark spots, and uneven skin texture. The aforementioned methods may be non-therapeutic.

DETAILED DESCRIPTION OF THE DISCLOSURE

The present disclosure relates to stable cosmetic compositions that contain high amounts of ascorbic acid (vitamin C) and ceramides, products containing such cosmetic compositions, and methods for treating skin using the cosmetic compositions. Ascorbic acid is a naturally occurring antioxidant. It is an enhancer of the biosynthesis of collagen, which is the protein that provides shape and firmness to the skin. Because ascorbic acid leads to higher production of collagen, wrinkling in skin is minimized. In addition, ascorbic acid can decrease age spots by reversing hyperpigmentation in skin cells to a certain extent by inhibiting tyrosinase activity.

Ceramides are a group of natural waxy, fatty substances in the skin, composed of sphingosine and lipids (fatty acids) bonded together. Ceramides make up about 50% of all skin lipids and are manufactured in the lower, living cells of the epidermis. In the stratum corneum layer, ceramides combine with cholesterol (another important lipid found in the skin) and fatty acids to form an ordered, tightly-packed, layered, sheet-like arrangement between the dead cells. Ceramides and cholesterol protect against moisture loss to keep skin youthful and supple, and support the skin's matrix, keeping it firm.

The cosmetic compositions of the instant disclosure typically include:
(a) about 5 to about 15 wt. % of ascorbic acid;
(b) one or more ceramides;
(c) about 0.1 to about 10 wt. % of panthenol;
(d) about 1 to about 20 wt. % of one or more monoalcohols having from 2 to 6 carbon atoms;
(e) about 1 to about 25 wt. % of one or more polyols;
(f) about 1 to about 25 wt. % of one or more fatty compounds;
(g) one or more emulsifiers;
(h) optionally, one or more cationic surfactants; and
(i) water;
wherein the weight percentages are based on the total weight of the cosmetic composition and the cosmetic composition has a viscosity of about 5,000 cP to 50,000 cP at 25° C.

The components of the cosmetic composition can be combined to form an emulsion, including, for example oil-in-water (hereafter "O/W"), water-in-oil (hereafter "W/O"), and oil-in-alcohol emulsions. In one embodiment, the composition is an oil-in-water emulsion. The oil phase may comprise about 2.5 to about 20 wt. %, based on the total weight of the cosmetic composition. For example, the amount of oil phase may be about 3 to about 19 wt. %, about 4 to about 17 wt. %, about 5 to about 15 wt. %, about 6 to about 14 wt. %, or about 7 to about 13% wt. %, including ranges and sub-ranges therebetween, based on the total weight of the composition. Additionally or alternatively, the amount of oil phase may be 3 to 19 wt. %, 4 to 17 wt. %, 5 to 15 wt. %, 6 to 14 wt. %, or 7 to 13% wt. %, including ranges and sub-ranges therebetween, based on the total weight of the composition. In one embodiment, the amount of oil phase may be 10% or about 10% of the total weight of the cosmetic composition.

The oil phase of cosmetic compositions may include ceramides and one or more fatty compounds. A substantial portion of the ceramides, such as a majority or essentially the entirety of the ceramides, may reside in the oil phase of the emulsion. As discussed above, it is believed that the panthenol and monoalchol(s) advantageously facilitate the stabilization of the ceramides in the emulsion, although the cosmetic composition in at least one instance contains an amount of oil phase and emulsifier that is lower than many commercially available products. The aqueous phase of the cosmetic composition may include an amount of ascorbic acid. For instance, a majority or essentially the entirety of ascorbic acid of the cosmetic composition may reside in the aqueous phase.

Suitable components, such as those listed below, may be included or excluded from the formulations for the cosmetic compositions depending on the specific combination of other components, the form of the cosmetic compositions, and/or the use of the formulation (e.g., a lotion, a serum, gel, cream, etc.).

Ascorbic Acid

The cosmetic compositions include ascorbic acid. For example, the cosmetic compositions may include an amount of ascorbic acid ranging from about 1.0 wt. % to about 30 wt. %, about 2.5 wt. % to about 25 wt. %, about 3.5 wt. % to about 20 wt. %, about 4.5 wt. % to about 20 wt. %, about 5 wt. % to about 15 wt. %, about 6 wt. % to about 14 wt. %, about 7 wt. % to about 13 wt. %, or about 8 wt. % to about 12 wt. %, including ranges and sub-ranges therebetween, based on the total weight of the composition. Additionally or alternatively, the amount of ascorbic acid may be 1.0 wt. % to 30 wt. %, 2.5 wt. % to 25 wt. %, 3.5 wt. % to 20 wt. %, 4.5 wt. % to 20 wt. %, 5 wt. % to 15 wt. %, 6 wt. % to 14 wt. %, 7 wt. % to 13 wt. %, or 8 wt. % to 12 wt. % including ranges and sub-ranges therebetween, based on the total weight of the composition. Likewise, in some embodiments, the cosmetic composition may include an amount of ascorbic acid that is about 20 wt. %, about 19 wt. %, about 18 wt. %, about 17 wt. %, about 16 wt. %, about 15 wt. %, about 14 wt. %, about 13 wt. %, about 12 wt. %, about 11 wt. %, about 10 wt. %, about 9 wt. %, about 8 wt. %, about 7 wt. %, about 6 wt. %, about 5 wt. %, about 4 wt. %, about 3 wt. %, about 2 wt. % or about 1 wt. %, based on the total weight of the composition. In one embodiment, the amount of ascorbic acid may be 10% or about 10% of the total weight of the cosmetic composition.

The ascorbic acid may be L-ascorbic acid, a mixture of L-ascorbic acid and R-ascorbic acid, and/or a racemic mixture. In one embodiment, the ascorbic acid comprises only L-ascorbic acid, essentially only L-ascorbic acid, and/or at least 75 wt. %, at least 85 wt. %, at least 90 wt. %, at least 95 wt. %, or at least 99 wt. % of L-ascorbic acid based on the total weight of ascorbic acid.

Ceramides

Ceramides are a family of waxy lipid molecules that are composed of sphingosine and a fatty acid. Ceramides include or may be chosen from ceramide 1, ceramide 2, ceramide 3, ceramide 4, ceramide 5, ceramide 1A, ceramide 6 II, ceramide AP, ceramide EOP, ceramide EOS, ceramide NP, ceramide NG, ceramide NS, ceramide AS, ceramide NS dilaurate, and a mixture thereof. In some instances, the ceramides include or may be chosen from ceramide-EOS, ceramide-NS, ceramide-NP, ceramide-EOH, ceramide-AS, ceramide-NH, ceramide-AP, ceramide-AH, Ceramide-OS, ceramide-OH, and a mixture thereof. In some cases, the cosmetic compositions may include ceramide EOP, optionally, in combination with one, two, or more other ceramides. For instance, in some instances, the cosmetic compositions includes a combination of ceramides, for example, a combination of ceramide EOP, ceramide NP, Ceramide AP.

The cosmetic composition may include an amount of ceramides that is greater than zero to about 10 wt. %, based on the total weight of the composition. For example, the total amount of ceramides may be from greater than zero to about 9 wt. %, greater than zero to about 8 wt. %, greater than zero to about 7 wt. %, greater than zero to about 6 wt. %, greater than zero to about 5 wt. %, greater than zero to about 4 wt. %, greater than zero to about 3 wt. %, greater than zero to about 2 wt. %, greater than zero to about 1 wt. %, based on the total weight of the cosmetic composition.

Panthenol

The cosmetic composition includes panthenol. Panthenol is an analog of pantothenic acid (vitamin $B_5$). The total amount of panthenol in the cosmetic composition may vary from about 0.1 to about 20 wt. % based on the total weight of the composition. For example, the total amount of panthenol may be 0.1 wt. % or more, 0.2 wt. % or more, 0.3 wt. % or more, 0.4 wt. % or more, 0.5 wt. % or more, 0.6 wt. % or more, 0.7 wt. % or more, 0.8 wt. % or more, 0.9 wt. % or more, 1.0 wt. % or more and/or 20 wt. % or less, 15 wt. % or less, 13 wt. % or less, 11 wt. % or less, 10 wt. % or less, 9 wt. % or less, 8 wt. % or less, 7 wt. % or less, 6 wt. % or less, 5 wt. % or less, 4 wt. % or less, 3 wt. % or less, 2.5 wt. % or less, including ranges and sub-ranges therebetween, based on the total weight of the composition.

In some instances, the total amount of panthenol may range from about 0.1 to about 10 wt. %, about 0.1 to about 9 wt. %, about 0.1 to about 8 wt. %, about 0.1 to about 7 wt. %, about 0.1 to about 6 wt. %, about 0.1 to about 5 wt. %, about 0.1 to about 4 wt. %, about 0.1 to about 3 wt. %, about 0.1 to about 2 wt. %, from about 0.5 to about 10 wt. %, about 0.5 to about 9 wt. %, about 0.5 to about 8 wt. %, about 0.5 to about 7 wt. %, about 0.5 to about 6 wt. %, about 0.5 to about 5 wt. %, about 0.5 to about 4 wt. %, about 0.5 to about 3 wt. %, or about 0.5 to about 2 wt. %, or from about 0.8 to about 10 wt. %, about 0.8 to about 9 wt. %, about 0.8 to about 8 wt. %, about 0.8 to about 7 wt. %, about 0.8 to about 6 wt. %, about 0.8 to about 5 wt. %, about 0.8 to about 4 wt. %, about 0.8 to about 3 wt. %, or about 0.8 to about 2 wt. %, including ranges and sub-ranges therebetween, based on the total weight of the composition. Additionally or alternatively, the total amount of panthenol may be from 0.1 to 10 wt. %, 0.1 to 9 wt. %, 0.1 to 8 wt. %, 0.1 to 7 wt. %, 0.1 to 6 wt. %, 0.1 to 5 wt. %, 0.1 to 4 wt. %, 0.1 to 3 wt. %, 0.1 to 2 wt. %, from 0.5 to 10 wt. %, 0.5 to 9 wt. %, 0.5 to 8 wt. %, 0.5 to 7 wt. %, 0.5 to 6 wt. %, 0.5 to 5 wt. %, 0.5 to 4 wt. %, 0.5 to 3 wt. %, or 0.5 to 2 wt. %, or from 0.8 to 10 wt. %, 0.8 to 9 wt. %, 0.8 to 8 wt. %, 0.8 to 7 wt. %, 0.8 to 6 wt. %, 0.8 to 5 wt. %, 0.8 to 4 wt. %, 0.8 to 3 wt. %, or 0.8 to 2 wt. %, including ranges and sub-ranges therebetween, based on the total weight of the composition.

Monoalcohol(s)

The cosmetic compositions include one or more monoalcohols having from 2 to 6 carbon atoms. For example, the one or more monoalcohols may include or be chosen from ethanol, propanol, butanol, pentanol, hexanol, isopropyl alcohol, cycohexanol, isobutyl alcohol, 2-methyl-2-butanol (2-methylbutan-2-ol), and a mixture thereof. In one instance, the one or more monoalcohols comprises ethanol and optionally one or more additional monoalcohols having from 2 to 6 carbon atoms. In another instance, the one or more monoalcohols includes only ethanol or essentially only ethanol.

The total amount of monoalcohols may vary but is typically from about 0.05 to about 70 wt. %, based on the total weight of the composition. For example, the total amount of monoalcohols is from about 0.05 to about 30 wt. %, about 0.5 to about 25 wt. %, about 1 to about 20 wt. %, about 1.5 to about 15 wt. %, about 2 to about 10 wt. %, about 2.5 to about 5 wt. %, including ranges and sub-ranges therebetween, based on the total weight of the composition. Additionally or alternatively, the cosmetic compositions may include an amount of ethanol ranging from about 0.05 to about 30 wt. %, about 0.5 to about 25 wt. %, about 1 to about 20 wt. %, about 1.5 to 15 wt. %, about 2 to 10 wt. %, about 2.5 to 5 wt. %, including ranges and sub-ranges therebetween, based on the total weight of the composition. The amount of ethanol in the cosmetic composition may be 0.05 to 30 wt. %, 0.5 to 25 wt. %, 1 to 20 wt. %, 1.5 to 15 wt. %, 2 to 10 wt. %, 2.5 to 5 wt. %, including ranges and sub-ranges therebetween, based on the total weight of the composition. In one instance, the cosmetic composition includes 3 wt. % or about 3 wt. % of ethanol.

Polyol(s)

The cosmetic composition may include one or more polyols. The one or more polyols may be chosen from polyols having from 2 to 15 carbon atoms and at least two hydroxyl groups. Exemplary polyols that may be used in the cosmetic composition include and/or may be chosen from alkanediols such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; sorbitol; sorbitan; triacetin; and a mixture thereof.

The one or more polyols may be glycols or glycol ethers such as, e.g., monomethyl, monoethyl and monobutyl ethers of ethylene glycol, propylene glycol or ethers thereof such as, e.g., monomethyl ether of propylene glycol, butylene glycol, hexylene glycol, dipropylene glycol as well as alkyl ethers of diethylene glycol, e.g., monoethyl ether or monobutyl ether of diethylene glycol. In one instance, the one or more polyols include or are chosen from ethylene glycol, propylene glycol, butylene glycol, hexylene glycol, pentylene glycol, 1,3-propanediol, diethylene glycol, dipropylene glycol, caprylyl glycol, glycerin, and a mixture thereof. In another instance, the cosmetic composition includes or is chosen from caprylyl glycol, glycerin, and a mixture thereof.

In some instances, however, the cosmetic composition has an amount of propylene glycol and/or ethoxydiglycol that is less than about 10 wt. %, preferably less than about 9 wt. %, preferably less than about 8 wt. %, preferably less than about 7 wt. %, preferably less than about 6 wt. %, preferably less than about 5 wt. %, preferably less than about 4 wt. %, preferably less than about 3 wt. %, preferably less than about 2 wt. %, or preferably less than about 1 wt. %, based on the total weight of the cosmetic composition. The cosmetic composition may, alternatively, have an amount of propylene glycol and/or ethoxydiglycol that is less than 10 wt. %, preferably less than 9 wt. %, preferably less than 8 wt. %, preferably less than 7 wt. %, preferably less than 6 wt. %, preferably less than about 5 wt. %, preferably less than 4 wt. %, preferably less than 3 wt. %, preferably less than 2 wt. %, or preferably less than 1 wt. %, based on the total weight of the cosmetic composition. In one instance, the one or more polyols does not include propylene glycol and/or ethoxydiglycol, such that the cosmetic composition is free or essentially free of propylene glycol and/or ethoxydiglycol.

The total amount of polyols in the compositions may vary from, e.g., about 0.1 to about 25 wt. %, based on the total weight of the composition. For example, the total amount of polyols may be from about 0.1 to about 25 wt. %, about 0.1 to about 20 wt. %, from about 0.1 to about 15 wt. %, about 0.1 to about 10 wt. %, about 0.1 to about 8 wt. %, about 0.1 to about 6 wt. %, from about 0.5 to about 25 wt. % about 0.5 to about 20 wt. %, about 0.5 to about 15 wt. %, about 0.5 to about 10 wt. %, about 0.5 to about 8 wt. %, about 0.5 to 6 wt. %, from about 1 to about 25 wt. %, about 1 to about 20 wt. %, about 1 to about 15 wt. %, about 1 to about 10 wt. %, about 1 to about 8 wt. %, or about 1 to about 6 wt. %, from about 1.5 to about 25 wt. %, about 1.5 to about 20 wt. %, about 1.5 to about 15 wt. %, about 1.5 to about 10 wt. %, about 1.5 to about 8 wt. %, or about 1.5 to about 6 wt. %, from about 2 to about 25 wt. %, about 2 to about 20 wt. %, about 2 to about 15 wt. %, about 2 to about 10 wt. %, about 2 to about 8 wt. %, or about 2 to about 6 wt. %, from about 2.5 to about 25 wt. %, about 2.5 to about 20 wt. %, about 2.5 to about 15 wt. %, about 2.5 to about 10 wt. %, about 2.5 to about 8 wt. %, or about 2.5 to about 6 wt. %, from about 3 to about 25 wt. %, about 3 to about 20 wt. %, about 3 to about 15 wt. %, about 3 to about 10 wt. %, about 3 to about 8 wt. %, or about 3 to about 6 wt. %, from about 3.5 to about 25 wt. %, about 3.5 to about 20 wt. %, about 3.5 to about 15 wt. %, about 3.5 to about 10 wt. %, about 3.5 to about 8 wt. %, or about 3.5 to about 6 wt. %, including ranges and sub-ranges therebetween, based on the total weight of the composition. Additionally or alternatively, the total amount of polyols may be from 0.1 to 25 wt. %, 0.1 to 20 wt. %, from 0.1 to 15 wt. %, 0.1 to 10 wt. %, 0.1 to 8 wt. %, 0.1 to 6 wt. %, from 0.1 to 25 wt. %, 0.5 to 20 wt. %, 0.5 to 15 wt. %, 0.5 to 10 wt. %, 0.5 to 8 wt. %, 0.5 to 6 wt. %, from 1 to 25 wt. %, 1 to 20 wt. %, 1 to 15 wt. %, 1 to 10 wt. %, 1 to 8 wt. %, or 1 to 6 wt. %, from 1.5 to 25 wt. %, 1.5 to 20 wt. %, 1.5 to 15 wt. %, 1.5 to 10 wt. %, 1.5 to 8 wt. %, or 1.5 to 6 wt. %, from 2 to 25 wt. %, 2 to 20 wt. %, 2 to 15 wt. %, 2 to 10 wt. %, 2 to 8 wt. %, or 2 to 6 wt. %, from 2.5 to 25 wt. %, 2.5 to 20 wt. %, 2.5 to 15 wt. %, 2.5 to 10 wt. %, 2.5 to 8 wt. %, or 2.5 to 6 wt. %, from 3 to 25 wt. %, 3 to 20 wt. %, 3 to 15 wt. %, 3 to 10 wt. %, 3 to 8 wt. %, or 3 to 6 wt. %, from 3.5 to 25 wt. %, 3.5 to 20 wt. %, 3.5 to 15 wt. %, 3.5 to 10 wt. %, 3.5 to 8 wt. %, or 3.5 to 6 wt. %, including ranges and sub-ranges therebetween, based on the total weight of the composition.

Fatty Compounds

The cosmetic composition may include one or more fatty compounds, which may be liquid or solid at room temperature and at atmospheric pressure (25° C., 1 atm). Fatty compounds are typically organic compounds that are not soluble in water at normal temperature (25° C.) and at atmospheric pressure (750 mmHg) (solubility below 10%). In some instances, the solubility in water may be below 5%, below 1%, or below 0.1%.

The total amount of fatty compounds in the compositions may vary from, e.g., about 0.1 to about 25 wt. %, based on the total weight of the composition. For example, the total amount of fatty compounds may be from about 0.1 to about 25 wt. %, about 0.1 to about 20 wt. %, from about 0.1 to about 15 wt. %, about 0.1 to about 10 wt. %, about 0.1 to about 8 wt. %, about 0.1 to about 6 wt. %, from about 0.5 to about 25 wt. % about 0.5 to about 20 wt. %, about 0.5 to about 15 wt. %, about 0.5 to about 10 wt. %, about 0.5 to about 8 wt. %, about 0.5 to 6 wt. %, from about 1 to about 25 wt. %, about 1 to about 20 wt. %, about 1 to about 15 wt. %, about 1 to about 10 wt. %, about 1 to about 8 wt. %, or about 1 to about 6 wt. %, from about 1.5 to about 25 wt. %, about 1.5 to about 20 wt. %, about 1.5 to about 15 wt. %, about 1.5 to about 10 wt. %, about 1.5 to about 8 wt. %, or about 1.5 to about 6 wt. %, from about 2 to about 25 wt. %, about 2 to about 20 wt. %, about 2 to about 15 wt. %, about 2 to about 10 wt. %, about 2 to about 8 wt. %, or about 2 to about 6 wt. %, from about 2.5 to about 25 wt. %, about 2.5 to about 20 wt. %, about 2.5 to about 15 wt. %, about 2.5 to about 10 wt. %, about 2.5 to about 8 wt. %, or about 2.5 to about 6 wt. %, from about 3 to about 25 wt. %, about 3 to about 20 wt. %, about 3 to about 15 wt. %, about 3 to about 10 wt. %, about 3 to about 8 wt. %, or about 3 to about 6 wt. %, from about 3.5 to about 25 wt. %, about 3.5 to about 20 wt. %, about 3.5 to about 15 wt. %, about 3.5 to about 10 wt. %, about 3.5 to about 8 wt. %, or about 3.5 to about 6 wt. %, including ranges and sub-ranges therebetween, based on the total weight of the composition. Additionally or alternatively, the total amount of fatty compounds may be from 0.1 to 25 wt. %, 0.1 to 20 wt. %, from 0.1 to 15 wt. %, 0.1 to 10 wt. %, 0.1 to 8 wt. %, 0.1 to 6 wt. %, from 0.1 to 25 wt. %, 0.5 to 20 wt. %, 0.5 to 15 wt. %, 0.5 to 10 wt. %, 0.5 to 8 wt. %, 0.5 to 6 wt. %, from 1 to 25 wt. %, 1 to 20 wt. %, 1 to 15 wt. %, 1 to 10 wt. %, 1 to 8 wt. %, or 1 to 6 wt. %, from 1.5 to 25 wt. %, 1.5 to 20 wt. %, 1.5 to 15 wt. %, 1.5 to 10 wt. %, 1.5 to 8 wt. %, or 1.5 to 6 wt. %, from 2 to 25 wt. %, 2 to 20 wt. %, 2 to 15 wt. %, 2 to 10 wt. %, 2 to 8 wt. %, or 2 to 6 wt. %, from 2.5 to 25 wt. %, 2.5 to 20 wt. %, 2.5 to 15 wt. %, 2.5 to 10 wt. %, 2.5 to 8 wt. %, or 2.5 to 6 wt. %, from 3 to 25 wt. %, 3 to 20 wt. %, 3 to 15 wt. %, 3 to 10 wt. %, 3 to 8 wt. %, or 3 to 6 wt. %, from 3.5 to 25 wt. %, 3.5 to 20 wt. %, 3.5 to 15 wt. %, 3.5 to 10 wt. %, 3.5 to 8 wt. %, or 3.5 to 6 wt. %, including ranges and sub-ranges therebetween, based on the total weight of the composition.

Non-limiting examples of fatty compounds of the cosmetic composition include or may be chosen from oils, mineral oil, fatty alcohols, fatty acids, fatty alcohol derivatives, fatty acid derivatives (e.g., alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), glyceryl esters (glycerol esters), alkyl ethers of fatty alcohols, fatty acid esters of alkyl ethers of fatty alcohols, fatty acid esters of alkoxylated fatty alcohols, fatty acid esters of alkyl ethers of alkoxylated fatty alcohols, esters of fatty alcohols, hydroxy-substituted fatty acids, waxes, triglyceride compounds, lanolin, and a mixture thereof. In some instances, the one or more fatty compound may comprise or be chosen from fatty alcohols, fatty acids, esters of fatty acids, and/or esters of fatty alcohols (e.g., cetyl palmitate, cetyl stearate, myristyl myristate, myristyl stearate, cetyl myristate, and stearyl stearate (a mixture of which is referred to as "cetyl esters")). Additionally or alternatively, the one or more fatty compounds may include or be chosen from hydrocarbons, fatty alcohols, fatty alcohol derivatives, fatty acids, fatty acid derivatives, fatty esters, fatty ethers, oils, waxes, etc. In one instance, the one or more fatty compounds is a hydrocarbon that is linear, branched, and/or cyclical, such as cyclic $C_6$-$C_{16}$ alkanes, hexane, undecane, dodecane, tridecane, and isoparaffins, for instance isohexadecane, isododecane and isodecane. Additionally, the linear or branched hydrocarbons may be composed only of carbon and hydrogen atoms of mineral, plant, animal or synthetic origin with more than 16 carbon atoms, such as volatile or non-volatile liquid paraffins, petroleum jelly, liquid petroleum jelly, polydecenes, hydrogenated polyisobutene, and squalane.

Fatty Alcohols

The one or more fatty compounds may be glycerolated and/or oxyalkylenated, may include from 8 to 30 carbon atoms, and may be saturated or unsaturated. The fatty alcohols useful herein include those having from about 8 to about 30 carbon atoms, from about 12 to about 22 carbon atoms, and from about 14 to about 22 carbon atoms. These fatty alcohols can be straight or branched chain alcohols and can be saturated or unsaturated. Nonlimiting examples of fatty alcohols include decyl alcohol, undecyl alcohol, dodecyl alcohol, myristyl alcohol, cetyl alcohol, stearyl alcohol, isostearyl alcohol, isocetyl alcohol, behenyl alcohol, linalool, oleyl alcohol, cis4-t-butylcyclohexanol, myricyl alcohol and a mixture thereof. In some cases, the fatty alcohols comprise at least one of or may be chosen from myristyl alcohol, cetyl alcohol, stearyl alcohol, isostearyl alcohol, oleyl alcohol, isotridecyl alcohol, and a mixture thereof.

The saturated liquid fatty alcohols may be branched and optionally contain in their structure at least one aromatic or non-aromatic ring. In some instances, however, the fatty alcohols are acyclic. Non-limiting examples of liquid saturated fatty alcohols include octyldodecanol, isostearyl alcohol, and 2-hexyldecanol.

The unsaturated liquid fatty alcohol may include in their structure at least one double or triple bond. For example, the fatty alcohols may include several double bonds (such as 2 or 3 double bond), which may be conjugated or non-conjugated. The unsaturated fatty alcohols can be linear or branched and may be acyclic or include in their structure at least one aromatic or non-aromatic ring. Liquid unsaturated fatty alcohols may include or be chosen from oleyl alcohol, linoleyl alcohol, linolenyl alcohol and undecylenyl alcohol.

Non-limiting examples of solid fatty alcohols include linear or branched, saturated or unsaturated alcohols containing from 8 to 30 carbon atoms, for example, myristyl alcohol, cetyl alcohol, stearyl alcohol and their mixture, cetylstearyl alcohol.

Fatty Esters

The fatty compounds of the cosmetic composition may be liquid or solid fatty esters at 25° C., 1 atm. The fatty esters may include esters from a $C_6$-$C_{32}$ fatty acid and/or a $C_6$-$C_{32}$ fatty alcohol. For example, the fatty compounds may include or be chosen from fatty acid monoesters and diesters, polyol esters, polyglycerol esters, polyglycerol polyricinoleate, polyglycerol poly-12-hydroxystearate, polyglycerol dimerate isostearate, ethylhexanoate, polyglycerol esters, and a mixture thereof. These esters may be esters of saturated or unsaturated, linear or branched $C_1$-$C_{26}$ aliphatic mono or polyacids and of saturated or unsaturated, linear or branched $C_1$-$C_{25}$ aliphatic mono or polyalcohols, the total number of carbon atoms in the esters being greater than or equal to 10. In one instance, the fatty compounds comprise one or more fatty acid monoesters. For the esters of monoalcohols, at least one of the alcohol or the acid from which the esters result is branched. Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isononyl isononanoate, isodecyl neopentanoate and isostearyl neopentanoate.

In some instances, the fatty esters are cetyl esters, such as esters of saturated fatty acids and fatty alcohols. For example, the fatty esters may include or be chosen from cetyl palmitate, cetyl stearate, myristyl myristate, myristyl stearate, cetyl myristate, stearyl stearate, cetearyl ethylhexanoate, and mixtures thereof. In one instance, the fatty esters may be one or more of or chosen from isopropyl isostearate, n-propyl myristate, isopropyl myristate, hexyl laurate, hexadecyl isostearate, hexydecyl laurate, hexyldecyl octanoate, n-propyl palmitate, isopropyl palmitate, and mixtures thereof. In another instance, the fatty esters include or may be chosen from diisobutyl adipate, 2-hexyldecyl adipate, di-2-heptylundecyl adipate, monoisostearic acid N-alkyl glycol, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprate, triethyl citrate, 2-ethylhexyl succinate, isocetyl stearate, butyl stearate, diisopropyl sebacate, di-2-ethylhexyl sebacate, cetyl lactate, myristyl lactate, isopropyl palm itate, 2-ethylhexyl palm itate, 2-hexyldecyl palm itate, 2-heptylundecyl palm itate, cholesteryl 12-hydroxystearate, di pentaerythritol fatty acid ester, isopropyl myristate, octyldodecyl myristate, 2-hexyldecyl myristate, myristyl myristate, hexyldecyl dimethyloctanoate, ethyl laurate, hexyl laurate, diisostearyl malate, dicaprylyl carbonate, cetearyl ethylhexanoate, and mixtures thereof. In yet a further instance, the cosmetic composition includes one or more of or may have fatty compounds chosen from cetearyl alcohol, cetearyl ethylhexanoate, isopropyl myristate, and mixtures thereof.

Non-limiting examples of liquid fatty acid include triglyceride oils of plant or synthetic origin, such as liquid fatty acid triglycerides containing 6 to 30 carbon atoms, for instance heptanoic or octanoic acid triglycerides, or alternatively, e.g., sunflower oil, corn oil, soybean oil, marrow oil, grapeseed oil, sesame seed oil, hazelnut oil, apricot oil, macadamia oil, arara oil, castor oil, avocado oil, olive oil, rapeseed oil, coconut oil, wheatgerm oil, sweet almond oil, apricot oil, safflower oil, candlenut oil, coconut oil, camellina oil, tamanu oil, babassu oil and pracaxi oil, jojoba oil, shea butter oil, and mixtures thereof.

Non-limiting examples of solid fatty acid esters and/or fatty acid esters that may be mentioned include solid esters obtained from $C_9$-$C_{26}$ fatty acids and from $C_9$-$C_{25}$ fatty alcohols. Among these esters, mention may be made of octyldodecyl behenate, isocetyl behenate, cetyl lactate, stearyl octanoate, octyl octanoate, cetyl octanoate, decyl oleate, myristyl stearate, octyl palmitate, octyl pelargonate, octyl stearate, alkyl myristates such as cetyl myristate, myristyl myristate or stearyl myristate, and hexyl stearate.

Fatty Alcohol Derivatives

The cosmetic compositions may, in some instances, include fatty alcohol derivatives such as alkyl ethers of fatty alcohols, alkoxylated fatty alcohols, alkyl ethers of alkoxylated fatty alcohols, esters of fatty alcohols and a mixture thereof. Non-limiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof. Liquid fatty ethers may be chosen from liquid dialkyl ethers such as dicaprylyl ether. The non-liquid fatty ethers may also be chosen from dialkyl ethers and in particular dicetyl ether and distearyl ether, alone or as a mixture.

Esters of $C_4$-$C_{22}$ dicarboxylic or tricarboxylic acids and of $C_1$-$C_{22}$ alcohols and esters of monocarboxylic, dicarboxylic or tricarboxylic acids and of $C_4$-$C_{26}$ dihydroxy, trihydroxy, tetrahydroxy or pentahydroxy non-sugar alcohols may also be used. Mention may be made in particular of diethyl sebacate; diisopropyl sebacate; diisopropyl adipate; di-n-propyl adipate; triisopropyl citrate; glyceryl trilactate; glyceryl trioctanoate; neopentyl glycol diheptanoate; and diethylene glycol diisononanoate.

Fatty Acid Derivatives

The cosmetic compositions may, in some instances, include fatty acid derivatives. The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Nonlimiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof.

Emulsifiers

The cosmetic compositions described herein include one or more emulsifiers. For example, the emulsifier may be an amphoteric, anionic, cationic or nonionic emulsifier, used alone or as a mixture, and optionally with a co-emulsifier. The emulsifiers are chosen in an appropriate manner according to the emulsion to be obtained.

For W/O emulsions, examples of emulsifiers that may be mentioned include dimethicone copolyols, such as the mixture of cyclomethicone and dimethicone copolyol sold under the trade name DC 5225 C by the company Dow Corning, and alkyl dimethicone copolyols such as the lauryl dimethicone copolyol sold under the name Dow Corning 5200 Formulation Aid by the company Dow Corning, and the cetyl dimethicone copolyol sold under the name Abil EM 90™ by the company Goldschmidt.

For O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof.

The one or more emulsifiers may be oxyalkylenated organosiloxane emulsifiers. The oxyalkylenated organosiloxane emulsifiers may be fully or partially crosslinked and/or be elastomeric or non-elastomeric. They are sometimes referred to as "emulsifying elastomers" because of they have both elastomeric and emulsifying properties. In some instances, the one or more emulsifiers include an oganosiloxane emulsifier, including crosslinked organosiloxane emulsifiers. For example, the cosmetic compositions may comprise one or more crosslinked organosiloxane emulsifier including or chosen from dimethicone/dimethicone PEG/PPG 15 crosspolymer, dimethicone PEG-10 crosspolymer, dimethicone PEG-10/15 crosspolymer, dimethicone PEG-15 crosspolymer, dimethicone polyglycerin-3 crosspolymer, dimethicone PPG-20 crosspolymer, dimethiconol/methylsilanol/silicate crosspolymer; dimethiconol/silicate crosspolymer, lauryl dimethicone PEG-15 crosspolymer, lauryl dimethicone polyglycerin-3 crosspolymer, PEG-8 dimethicone polysorbate-20 crosspolymer, PEG-10 dimethicone/vinyl dimethicone crosspolymer, PEG-10 lauryl dimethicone crosspolymer, PEG-15/lauryl dimethicone crosspolymer, PEG-15 laurylpolydimethylsiloxyethyl crosspolymer, and mixtures thereof.

In another instance, the cosmetic compositions include one or more linear organosiloxane emulsifier chosen from cyclotetrasiloxane (and) cyclopentasiloxane (and) PEG/PPG-18 dimethicone, cyclopentasiloxane (and) PEG/PPG-18/18 dimethicone; PEG/PPG-18/18 dimethicone; lauryl PEG/PPG-18/18 methicone; cetyl PEG/PPG-14/14 dimethicone; bis-cetyl PEG/PPG-14/14 dimethicone; cetyl PEG/PPG-10/1 dimethicone; PEG-11 methyl ether dimethicone; PEG/PPG-20/22 butyl ether dimethicone; PEG-9 dimethicone; PEG-3 dimethicone; PEG-9 methyl ether dimethicone; PEG-10 dimethicone; lauryl PEG-9 polydimethylsiloxyethyl dimethicone; and mixtures thereof.

The cosmetic composition may, in some instances, include an oxyalkylenated organosiloxane emulsifier. The oxyalkylenated organosiloxane emulsifier may have a structure in accordance with the following general formula:

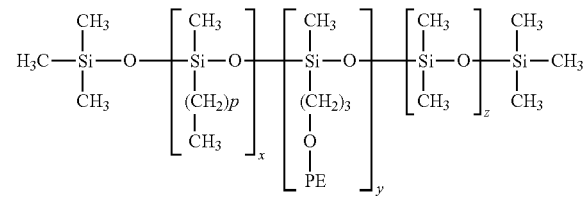

wherein p is 0-40 (the range including all numbers between and subranges such as 2, 3, 4, 13, 14, 15, 16, 17, 18, etc.), and PE is (—C2H4O)a-(—C3H6O)b-H wherein a is 0-25, b is 0-25 with the proviso that both a and b cannot be 0 simultaneously, x, y, and z are each independently ranging from 0 to 1 million with the proviso that x and y cannot be 0 simultaneously. In some instances, x, y, z, a, and b are such that the molecular weight of the polymer ranges from about 5,000 to about 500,000, from about 10,000 to 100,000, or is about 50,000, and the polymer is generically referred to as dimethicone copolyol. In additional instances, p is such that the long chain alkyl is cetyl or lauryl, and the compound is called, generically, cetyl dimethicone copolyol or lauryl dimethicone copolyol respectively. In some cases, the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or ether, such as methyl ether, ethyl ether, propyl ether, butyl ether, and the like.

The oxyalkylenated organosiloxane emulsifier may alternatively have a structure in accordance with the following general formula:

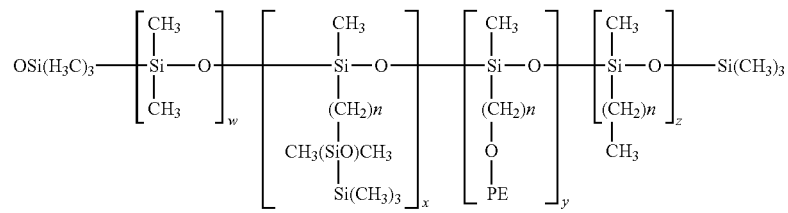

wherein each n is independently 0-100 with the proviso that there must be at least one PE radical. In some instances, where each n independently ranges from about 2 to 30, and PE (—C2H4O)a-(—C3H6O)b-H wherein a is 0-25, b is 0-25 with the proviso that both a and b cannot simultaneously be 0; and wherein w, x, y, and z are each independently 0 to 1,000,000 with the proviso that there is at least one PE. In some embodiments, the organosiloxane emulsifier is lauryl PEG-9 Polydimethylsiloxyethyl Dimethicone. Oxyalkylenated organosiloxane emulsifiers disclosed in U.S. Pat. No. 9,095,543 may be useful in the cosmetic compositions. U.S. Pat. No. 9,095,543 is incorporated herein by reference in its entirety for all purposes.

Further examples of organosiloxane emulsifiers include those having C.T.F.A. names Bis-Butyldimethicone Polyglyceryl-3; Bis-PEG/PPG-14/14 Dimethicone; Bis-butyldimethicone Polyglyceryl-3; Bis-isobutyl PEG/PPG-10/7 Dimethicone copolymer; Bis-PEG/PPG-18/6 Dimethicone; Bis-PEG/PPG-20/20 Dimethicone; Bis-PEG/PPG-16/16 PEG/PPG-16/16 Dimethicone; Bis(PPG-7 Undeceneth-21-Dimethicone; Cetyl Dimethicone PEG-7 Acetate; Cetyl PEG-8 Dimethicone; Cetyl PEG/PPG-15/16 Butyl Ether Dimethicone; Cetyl PEG/PPG-15/15 Butyl Ether Dimethicone; Cetyl PEG/PPG-7/3 Dimethicone; Cetyl PEG/PPG-10/1 Dimethicone; Dimethicone PEG-15 Acetate; Dimethicone PEG-7 Cocoate; Dimethicone PEG-7 Phosphate; Dimethicone PEG-10 Phosphate; Dimethicone PEG/PPG-7/4 Phosphate; Dimethicone PEG/PPG-12/4 Phosphate; Dimethicone PEG-7 Undecylenate; Lauryl Dimethicone PEG-10 Phosphate; Isopolyglyceryl-3 Dimethicone; Isopolyglyceryl-3 Dimethiconol; Isostearyl Carboxyldecyl PEG-8 Dimethicone; Lauryl Methicone PEG-10 Phosphate; Lauryl PEG-8 Dimethicone; Lauryl PEG-10 Methyl Ether Dimethicone; Lauryl PEG/PPG-18/18 Methicone; PEG-6 Methyl Ether Dimethicone; PEG-7 Methyl Ether Dimethicone; PEG-9 Methyl Ether Dimethicone; PEG-10 Methyl Ether Dimethicone; PEG-11 Methyl Ether Dimethicone; PEG-11 Methyl Ether Dimethicone; PEG-32 Methyl Ether Dimethicone; PEG-PEG/PPG-28/21 Acetate Dimethicone; PEG/PPG-22/22 Butyl Ether Dimethicone; PEG/PPG-23/23 Butyl Ether Dimethicone; PEG/PPG-24/18 Butyl Ether Dimethicone; PEG/PPG-3/10 Dimethicone; PEG/PPG-4/12 Dimethicone; PEG/PPG-6/11 Dimethicone; PEG/PPG-8/14 Dimethicone; PEG/PPG-12/16 Dimethicone; PEG/PPG-12/18 Dimethicone; PEG/PPG-14/4 Dimethicone; PEG/PPG-15/5 Dimethicone; PEG/PPG-15/15 Dimethicone; PEG/PPG-16/2 Dimethicone; PEG/PPG-16/8 Dimethicone; PEG/PPG-17/18 Dimethicone; PEG/PPG-18/12 Dimethicone; PEG/PPG-19/19 Dimethicone; PEG/PPG-20/6 Dimethicone; PEG/PPG-20/15 Dimethicone; PEG/PPG-20/20 Dimethicone; PEG/PPG-20/29 Dimethicone; PEG/PPG-22/23 Dimethicone; PEG/PPG-22/24 Dimethicone; PEG/PPG-25/25 Dimethicone; PEG/PPG-27/27 Dimethicone; PEG/PPG-30/10 Dimethicone; PEG/PPG-10/3 Oleyl Ether Dimethicone; PEG-8 trisiloxane; Polyglyceryl-3 Polydimethylsiloxyethyl Dimethicone; PPG-12 Butyl Ether Dimethicone; Silicone Quaternium-17; TEA-Dimethicone PEG-7 Phosphate; and mixtures thereof.

Further examples of commercial linear organosiloxane emulsifiers are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

Further examples of crosslinked organosiloxane emulsifiers include, but are not limited to Dimethicone/dimethicone PEG/PPG 15 crosspolymer; Dimethicone PEG-10 crosspolymer; Dimethicone PEG-10/15 Crosspolymer; Dimethicone PEG-15 Crosspolymer; Dimethicone Polyglycerin-3 Crosspolymer; Dimethicone PPG-20 Crosspolymer; Dimethiconol/Methylsilanol/Silicate Crosspolymer; Dimethiconol/Silicate Crosspolymer; Lauryl Dimethicone PEG-15 Crosspolymer; Lauryl Dimethicone Polyglycerin-3 Crosspolymer; PEG-8 Dimethicone Polysorbate-20 Crosspolymer; PEG-10 Dimethicone/Vinyl Dimethicone Crosspolymer; PEG-10 Lauryl Dimethicone Crosspolymer; PEG-15/Lauryl Dimethicone Crosspolymer; and PEG-15 Laurylpolydimethylsiloxyethyl Crosspolymer.

The one or more emulsifiers may, in some instances, be polyoxyalkylenated silicone elastomers, such as, e.g., those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer. The polyglycerolated silicone elastomers may include or be chosen from dimethicone/polyglycerin-3 crosspolymer dispersed in dimethicone; or lauryl dimethicone/polyglycerin-3 crosspolymer dispersed in a variety of solvents such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

The emulsifiers may, in some instances, be nonionic a surfactant, such as one chosen from: alkanolamides; alkyl polyglucosides; polyoxyalkylenated nonionic surfactants; polyglycerolated nonionic surfactants; ethoxylated fatty esters; alcohols, alpha-diols, alkylphenols and esters of fatty acids, being ethoxylated, propoxylated or glycerolated; copolymers of ethylene oxide and/or of propylene oxide; condensates of ethylene oxide and/or of propylene oxide with fatty alcohols; polyethoxylated fatty amides; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof.

Additional nonionic surfactants that may, in some instances, be suitable include, e.g., alcohols, alpha-diols, alkylphenols and esters of fatty acids, being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol (C6-C24) alkylpolyglycosides; N—($C_6$-$C_{24}$)alkylglucamine derivatives, amine oxides such as (C10-C14)alkylamine oxides or N—($C_{10}$-$C_{14}$)acylaminopropylmorpholine oxides; and mixtures thereof.

In some cases, the nonionic surfactant may be chosen from esters of polyols with fatty acids with a saturated or unsaturated chain containing for example from 8 to 24 carbon atoms, and alkoxylated derivatives thereof; polyethylene glycol esters of a $C_8$-$C_{24}$; sorbitol esters of a $C_8$-$C_{24}$;

sugar (sucrose, glucose, alkylglycose) esters of a $C_8$-$C_{24}$, preferably $C_{12}$-$C_{22}$, fatty acid or acids and alkoxylated derivatives thereof; ethers of sugar and a $C_8$-$C_{24}$, preferably $C_{12}$-$C_{22}$, fatty alcohol or alcohols; and mixtures thereof. In one instance, the nonionic surfactant is an ethoxylated fatty ester chosen from adducts of ethylene oxide with esters of lauric acid, palmitic acid, stearic acid or behenic acid, and mixtures thereof. Examples of ethoxylated fatty esters that may be suitable include those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

The nonionic surfactant may be chosen from glyceryl esters of fatty acids, glyceryl stearate (glyceryl mono-, di- and/or tristearate) (CTFA name: glyceryl stearate); glyceryl ricinoleate; glyceryl esters of $C_8$-$C_{24}$ alkoxylated fatty acids, such as polyethoxylated glyceryl stearate (glyceryl mono-, di- and/or tristearate), and PEG-20 glyceryl stearate; and mixtures thereof.

In some instances, the cosmetic composition may include an emulsifier such as dimers surfactants named "gemini surfactants," which may have two surfactant moieties identical or different, and constituted by a hydrophilic head group and a lipophilic group linked to each other through the head groups, thanks to a spacer. For example, the one or more emulsifiers may include or be chosen from those sold by Sasol company under the name CERALUTIOM, for example, CERALUTION H: Behenyl Alcohol, Glyceryl Stearate, Glyceryl Stearate Citrate et Sodium Dicocoyl ethylenediamine PEG-15 Sulfate, CERALUTION F: Sodium Lauroyl Lactylate et Sodium Dicocoyl ethylenediamine PEG-15 Sulfate, CERALUTION C: Aqua, Capric/Caprylic triglyceride, Ceteareth-25, Sodium Dicocoyl ethylenediamine PEG-15 Sulfate, Sodium Lauroyl Lactylate, Behenyl Alcohol, Glyceryl Stearate, Glyceryl Stearate Citrate, Gum Arabic, Xanthan Gum, Phenoxyethanol, Methylparaben, Ethylparaben, Butylparaben, Isobutylparaben. In one embodiment, the emulsifier of the cosmetic composition consists of sodium lauroyl lactylate or consists essentially of sodium lauroyl lactylate. In another embodiment, the emulsifier(s) of the cosmetic composition includes sodium lauroyl lactylate with one or more additional emulsifiers, such as a nonionic emulsifier or an anionic emulsifier.

The total amount of emulsifiers in the compositions may vary from, e.g., about 0.001 to about 25 wt. %, based on the total weight of the composition. For example, the total amount of fatty compounds may be from about 0.001 to about 25 wt. %, about 0.001 to about 20 wt. %, from about 0.001 to about 15 wt. %, about 0.001 to about 10 wt. %, about 0.001 to about 8 wt. %, about 0.001 to about 6 wt. %, from about 0.005 to about 25 wt. % about 0.005 to about 20 wt. %, about 0.005 to about 15 wt. %, about 0.005 to about 10 wt. %, about 0.005 to about 8 wt. %, about 0.005 to 6 wt. %, from about 0.01 to about 25 wt. %, about 0.01 to about 20 wt. %, about 0.01 to about 15 wt. %, about 0.01 to about 10 wt. %, about 0.01 to about 8 wt. %, or about 0.01 to about 6 wt. %, from about 0.05 to about 25 wt. %, about 0.05 to about 20 wt. %, about 0.05 to about 15 wt. %, about 0.05 to about 10 wt. %, about 0.05 to about 8 wt. %, or about 0.05 to about 6 wt. % including ranges and sub-ranges therebetween, based on the total weight of the composition. In one instance, the total amount of emulsifiers in the cosmetic composition are typically in an amount from 0.5, 0.6, 0.7, 0.8, 0.9 or 1.0 wt. % to 5, 6, 7, 8, 9, or 10 wt. %.

The cosmetic composition may be formulated to have a lower amount of emulsifier(s) than typical commercial products. For example, the cosmetic composition may have a total amount of emulsifiers ranging from about 0.001 to about 6 wt. %, about 0.001 to about 5 wt. %, from about 0.001 to about 4 wt. %, about 0.001 to about 3 wt. %, about 0.001 to about 2 wt. %, about 0.001 to about 1 wt. %, from about 0.005 to 6 wt. %, about 0.005 to about 5 wt. % about 0.005 to about 4 wt. %, about 0.005 to about 3 wt. %, about 0.005 to about 2 wt. %, about 0.005 to about 1 wt. %, from about 0.01 to about 6 wt. %, about 0.01 to about 5 wt. %, about 0.01 to about 4 wt. %, about 0.01 to about 3 wt. %, about 0.01 to about 2 wt. %, or about 0.01 to about 1 wt. %, from about 0.05 to about 6 wt. %, about 0.05 to about 5 wt. %, about 0.05 to about 4 wt. %, about 0.05 to about 3 wt. %, about 0.05 to about 2 wt. %, or about 0.05 to about 1 wt. % including ranges and sub-ranges therebetween, based on the total weight of the composition. Additionally or alternatively, the cosmetic composition may have a total amount of emulsifiers ranging from 0.001 to 6 wt. %, 0.001 to 5 wt. %, from 0.001 to 4 wt. %, 0.001 to 3 wt. %, 0.001 to 2 wt. %, 0.001 to 1 wt. %, from 0.005 to 6 wt. %, 0.005 to 5 wt. % 0.005 to 4 wt. %, 0.005 to 3 wt. %, 0.005 to 2 wt. %, 0.005 to 1 wt. %, from 0.01 to 6 wt. %, 0.01 to 5 wt. %, 0.01 to 4 wt. %, 0.01 to 3 wt. %, 0.01 to 2 wt. %, or 0.01 to 1 wt. %, from 0.05 to 6 wt. %, 0.05 to 5 wt. %, 0.05 to 4 wt. %, 0.05 to 3 wt. %, 0.05 to 2 wt. %, or 0.05 to 1 wt. % including ranges and sub-ranges therebetween, based on the total weight of the composition.

Cationic Surfactant

The cosmetic compositions may optionally include one or more cationic surfactants. As used herein, the term "cationic surfactant" refers to a surfactant that may be positively charged when it is contained in the cosmetic compositions according to the disclosure. This surfactant may bear one or more positive permanent charges or may contain one or more functional groups that are cationizable in the cosmetic composition according to the disclosure. Non-limiting examples of cationic surfactants that may be in the cosmetic composition include or may be chosen from behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, hexadecyltrimethyl ammonium bromide, and a mixture thereof.

In one instance, the cationic surfactants include or may be chosen from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and a mixture thereof.

The cationic surfactant(s) may optionally be chosen from polyoxyalkylenated, primary, secondary or tertiary fatty amines, or salts thereof, and quaternary ammonium salts, and mixtures thereof. In some cases it is useful to use salts such as chloride salts of the quaternary ammonium compounds. The quaternary ammonium compounds may be fatty amines having, e.g., at least one $C_8$-$C_{30}$ hydrocarbon-based chain. Examples of quaternary ammonium salts include those having a structure in accordance with the general formula provided below:

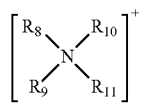

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms and preferably from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; X is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Exemplary quaternary ammonium salts having a structuring in accordance with the above formula include tetraalkylammonium salts (e.g., dialkyldimethylammonium or alkyltrimethylammonium salts in which the alkyl group contains approximately from 12 to 22 carbon atoms, behenyltrimethylammonium, distearyldimethylammonium, cetyltrimethylammonium or benzyldimethylstearylammonium salts), oleocetyldimethylhydroxyethylammonium salts, palmitylamidopropyltrimethylammonium salts, stearamidopropyltrimethylammonium salts and stearamidopropyldimethylcetearylammonium salts.

Additional examples of quaternary ammonium salts include quaternary ammonium salt of imidazoline, such as those having a structure in accordance with the general formula provided below:

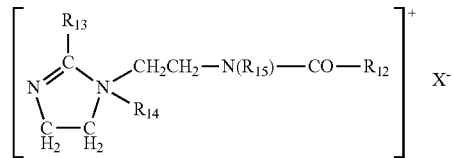

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, alkyl sulfates, alkyl- or alkylarylsulfonates in which the alkyl and aryl groups preferably comprise, respectively, from 1 to 20 carbon atoms and from 6 to 30 carbon atoms. $R_{12}$ and $R_{13}$ preferably denote a mixture of alkenyl or alkyl groups containing from 12 to 21 carbon atoms, derived for example from tallow fatty acids, $R_{14}$ preferably denotes a methyl group, and $R_{15}$ preferably denotes a hydrogen atom.

Additional examples of quaternary ammonium salts include quaternary diammonium or triammonium salt, such as those having a structure in accordance with the general formula provided below:

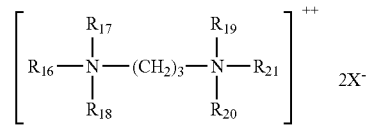

in which $R_{16}$ denotes an alkyl radical comprising approximately from 16 to 30 carbon atoms, which is optionally hydroxylated and/or interrupted with one or more oxygen atoms, $R_{17}$ is chosen from hydrogen or an alkyl radical comprising from 1 to 4 carbon atoms or a group $(R_{16a})(R_{17a})(R_{18a})N-(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms, and $X^-$ is an anion chosen from the group of halides, acetates, phosphates, nitrates and methyl sulfates. Such compounds are, for example, Finquat CT-P, sold by the company Finetex (Quaternium 89), and Finquat CT, sold by the company Finetex (Quaternium 75), In some instances, the cationic surfactant is preferably selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, and mixtures thereof. In other instances, the cationic surfactants are more preferably selected from cetrimonium chloride, behentrimonium chloride, behentrimonium methosulfate, stearamidopropyl dimethylamine, and a mixture thereof. In one instance, the cosmetic composition includes solely behentrimonium methosulfate or essentially solely behentrimonium methosulfate. In another instance, however, the cosmetic composition includes behentrimonium methosulfate and at least another cationic surfactant, such as, e.g., cetrimonium chloride, behentrimonium chloride, or a mixture thereof.

The cosmetic composition may include an amount of cationic surfactants that is greater than zero to about 15 wt. %, based on the total weight of the composition. For example, the total amount of cationic surfactant(s) may be from greater than zero to about 14 wt. %, greater than zero to about 12 wt. %, greater than zero to about 10 wt. %, greater than zero to about 8 wt. %, greater than zero to about 6 wt. %, greater than zero to about 5 wt. %, greater than zero to about 4 wt. %, greater than zero to about 3 wt. %, greater than zero to about 2 wt. %, greater than zero to about 1 wt. %, from about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %, from about 0.5 to about 10 wt. %, about 0.5 to about 8 wt. %, about 0.5 to about 5 wt. %, about 0.5 to about 4 wt. %, about 0.5 to about 3 wt. %, about 0.5 to about 2 wt. %, about 0.5 to about 1 wt. %, from about 1 to about 10 wt. %, about 1 to about 8 wt. %, about 1 to about 5 wt. %, about 1 to about 4 wt. %, or about 1 to about 3 wt. %, including ranges and sub-ranges therebetween, based on the total weight of the composition. Additionally or alternatively, the total amount of cationic surfactant(s) may be from greater than zero to 14 wt. %, greater than zero to 12 wt. %, greater than zero to 10 wt. %, greater than zero to 8 wt. %, greater than zero to 6 wt. %, greater than zero to 5 wt. %, greater than zero to 4 wt. %, greater than zero to 3 wt. %, greater than zero to 2 wt. %, greater than zero to 1 wt. %, from 0.1 to 8 wt. %, 0.1 to 6 wt. %, 0.1 to 5 wt. %, 0.1 to 4 wt. %, 0.1 to 3 wt. %, 0.1 to 2 wt. %, 0.1 to 1 wt. %, from 0.5 to 10 wt. %, 0.5 to 8 wt. %, 0.5 to 5 wt. %, 0.5 to 4 wt. %, 0.5 to 3 wt. %, 0.5 to 2 wt. %, 0.5 to 1 wt. %, from 1 to 10 wt. %, 1 to 8 wt. %, 1 to 5 wt. %, 1 to 4 wt. %, or 1 to 3 wt. %, including ranges and sub-ranges therebetween, based on the total weight of the cosmetic composition.

Thickening Agent(s)

The cosmetic compositions described herein may include one or more thickening agents. The amount of thickening agents may depend on the other components in cosmetic composition and desired viscosity for the cosmetic composition. For example, the cosmetic composition may include an amount of thickening agents such that the viscosity of the cosmetic composition is about 1,000 cP to about 100,000 cP, about 5,000 cP to about 50,000 cP, about 10,000 to about 50,000 cP, or about 15,000 cP to about 45,000 cP at a temperature of 25° C. using a Brookfield rheometer with a spindle number 5 at 20 revolutions per minute (RPM). Additionally or alternatively, the viscosity of the cosmetic composition may be 1,000 cP to 100,000 cP, 5,000 cP to 50,000 cP, 10,000 to 50,000 cP, or 15,000 cP to 45,000 cP at a temperature of 25° C. using a Brookfield rheometer with a spindle number 5 at 20 RPM.

The thickening agents may be in an amount of about 0.1 to about 20 wt. %, about 0.1 to about 10 wt. %, about 0.1 to about 9 wt. %, about 0.2 to about 9 wt. %, about 0.3 to about 9 wt. %, about 0.4 to about 8 wt. %, about 0.5 to about 5 wt. %, about 1 to about 20 wt. %, about 1 to about 5 wt. %, or about 1 to about 3 wt. %, including ranges and sub-ranges therebetween, based on the total weight of the cosmetic composition. Additionally or alternatively, the thickening agents may be in an amount of 0.1 to 20 wt. %, 0.1 to 10 wt. %, 0.1 to 9 wt. %, 0.2 to 9 wt. %, 0.3 to 9 wt. %, 0.4 to 8 wt. %, 0.5 to 5 wt. %, 1 to 20 wt. %, 1 to 5 wt. %, or 1 to 3 wt. %, including ranges and sub-ranges therebetween, based on the total weight of the cosmetic composition. Further, the amount of thickening agent(s) may be from 0.1, 0.2, 0.3, 0.4, 0.5, 0.6, 0.7, 0.8, 0.9, 1.0, or 1.5 wt. % to 2, 3, 4, 5, 6, 7, 8, 9, 10, 15, or 20 wt. %, including ranges and sub-ranges therebetween, based on the total weight of the cosmetic composition.

The one or more thickening agent may be xanthan gum, guar gum, biosaccharide gum, cellulose, acacia Seneca gum, sclerotium gum, agarose, pechtin, gellan gum, hyaluronic acid. Additionally, the one or more thickening agent may include polymeric thickeners chosen from ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer. In one instance, the cosmetic composition includes ammonium polyacryloyldimethyl taurate and/or sodium polyacrylate. In another instance, cosmetic composition includes at least one or is chosen from ammonium polyacryloyldimethyl taurate, xanthan gum, carbomer, and a mixture thereof.

Many thickening agents are water-soluble, and increase the viscosity of water or form an aqueous gel when the cosmetic composition of the invention is dispersed/dissolved in water. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water. Non-limiting examples of various types of thicken agents include:

Carboxylic Acid Polymers

In some instances, carboxylic acid polymer may be used in the cosmetic composition. Carboxylic acid polymer are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Examples of carboxylic acid polymers that may, in some instances, be included in the cosmetic compositions include one or more of or may be chosen from carbomers, which are homopolymers of acrylic acid crosslinked with allyl ethers of sucrose or pentaerytritol.

Commercially available carbomers include Carbopol®, 900 series from B.F. Goodrich (e.g., Carbopol® 954). In addition, other suitable carboxylic acid polymeric agents include Ultrez® 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol®, 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

Crosslinked Polyacrylate Polymers

The cosmetic compositions can optionally contain crosslinked polyacrylate polymers useful as thickeners or gelling agents including both cationic and nonionic polymers. Examples of crosslinked nonionic polyacrylate polymers and crosslinked cationic polyacrylate polymers that may be useful in some instances are those described in U.S. Pat. Nos. 5,100,660, 4,849,484, 4,835,206, 4,628,078 4,599,379 and EP 228,868, which are all incorporated herein by reference in their entirety.

Polyacrylamide Polymers

The cosmetic compositions can optionally contain polyacrylamide polymers, such as nonionic polyacrylamide polymers including substituted branched or unbranched polymers. Among these polyacrylamide polymers is the nonionic polymer given the CTFA designation polyacrylamide and isoparaffin and laureth-7, available under the Tradename Sepigel 305 from Seppic Corporation. Other polyacrylamide polymers that may be included in the cosmetic composition include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc. In one instance, the cosmetic composition includes thickening and texturizing gels of the type as exemplified by the product range called Lubrajel® from United Guardian. These gels have moisturizing, viscosifying, stabilizing properties.

Polysaccharides

In some instances, polysaccharides may be used in the cosmetic composition as a gelling agent. "Polysaccharides" refer to gelling agents that contain a backbone of repeating sugar (i.e., carbohydrate) units. Nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation. Other useful polysaccharides include scleroglucans comprising a linear chain of (1-3) linked glucose units with a (1-6) linked glucose every three units, a commercially available example of which is Clearogel™. CS11 from Michel Mercier Products Inc.

Gums

Other thickening and gelling agents that may be used, in some instances, include gums, which may be primarily derived from natural sources. Non-limiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

Additional examples of water-soluble thickeners include water-soluble natural polymers, water-soluble synthetic polymers, clay minerals, and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic heteropolysaccharide derived from callus of plants belonging to *Polyantes* sp. (for example, tuberous polysaccharide), proteins (for example, sodium casein, gelatin, albumin), chondroitin sulfate, and hyaluronic acid.

The cosmetic composition may include water-soluble synthetic polymers including, e.g., polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

Skin Active Agents

The cosmetic compositions may include one or more skin active agents, such as anti-aging agent, anti-wrinkle actives, anti-oxidants, humectants, moisturizing ingredients, depigmenting agents, and/or agents for treating oily skin etc. Non-limiting examples of the one or more skin active agents include adenosine, 2-[4-(2-hydroxyethyl)piperazin-1-yl]ethanesulfonic acid (HEPES), hyaluronic acid, lanolin, citric acid, malic acid, lactic acid, tartaric acid, salicylic acid, a retinoid, retinal, retinoic acid, a carotenoid, an amino acid, a protein, an enzyme, and a coenzyme. In some cases, the skin active agent is adenosine. In one embodiment, the cosmetic composition includes at least one humectant and at least one skin active agent chosen from moisturizing ingredients, anti-aging agents, depigmenting agents, anti-wrinkle agents, or agents for treating oily skin.

Examples of humectants and/or moisturizing ingredients include glycerol and its derivatives, urea and its derivatives, especially Hydrovance marketed by National Starch, lactic acid, hyaluronic acid, AHA, BHA, sodium pidolate, xylitol, serine, sodium lactate, ectoin and its derivatives, chitosan and its derivatives, collagen, plankton, an extract of *Imperata cylindra* sold under the name Moist 24 by Sederma, homopolymers of acrylic acid as Lipidure-HM of NOF Corporation, beta-glucan and in particular sodium carboxymethyl beta-glucan Mibelle-AG-Biochemistry, a mixture of oils passionflower, apricot, corn, and rice bran sold by Nestle under the name NutraLipids, a C-glycoside derivatives, in particular the C-13-D-xylopyranoside-2-hydroxypropane in the form of a solution at 30% by weight of active material in a water/propylene glycol mixture (60/40 wt %) as the product produced by the company Chimex under the trade name "Mexoryl SBB", a rose hip oil marketed by Nestle, a micro-algae extract *Prophyridium cruentum* enriched with zinc, marketed under the name by Vincience Algualane Zinc spheres of collagen and chondroitin sulfate of marine origin (Atelocollagen) sold by the company Engelhard Lyon under the name Marine Filling Spheres, hyaluronic acid spheres such as those marketed by Engelhard Lyon, and arginine.

Depigmenting agents that may be incorporated in the cosmetic composition include at least one of or may be chosen from alpha and beta arbutin, ferulic acid, lucinol and its derivatives, kojic acid, resorcinol and derivatives thereof, tranexamic acid and derivatives thereof, gentisic acid, homogentisic, methyl gentisate or homogentisate, dioic acid, D pantheteine calcium sulphonate, lipoic acid, ellagic acid, vitamin B3, linoleic acid and its derivatives, certain compounds derived from plants such as chamomile, bearberry, the aloe family (vera, ferox, bardensis), mulberry, skullcap, a water kiwi fruit (*Actinidia chinensis*) marketed by Gattefosse, an extract of *Paeonia suffruticosa* root, such as that sold by Ichimaru Pharcos under the name Liquid Botanpi Be an extract of brown sugar (*Saccharum officinarum*) such as molasses extract marketed by Taiyo Kagaku under the name Liquid Molasses, without this list being exhaustive. Particular depigmenting agents include alpha and beta arbutin, ferulic acid, kojic acid, resorcinol and derivatives, D pantheteine calcium sulfonate, lipoic acid, ellagic acid, vitamin B3, a water kiwi fruit (*Actinidia chinensis*) marketed by Gattefosse, an extract of *Paeonia suffruticosa* root, such as that sold by the company Ichimaru Pharcos under the name Botanpi Liquid B.

The cosmetic composition may include one or more anti-wrinkle actives. The term "anti-wrinkle active" refers to a natural or synthetic compound producing a biological effect, such as the increased synthesis and/or activity of certain enzymes, when brought into contact with an area of wrinkled skin, this has the effect of reducing the appearance of wrinkles and/or fine lines. Exemplary anti-wrinkle actives may be chosen from: desquamating agents, anti-glycation agents, inhibitors of NO-synthase, agents stimulating the synthesis of dermal or epidermal macromolecules and/or preventing their degradation, agents for stimulating the proliferation of fibroblasts and/or keratinocytes, or for stimulating keratinocyte differentiation reducing agents; muscle relaxants and/or dermo-decontracting agents, anti-free radical agents, and mixtures thereof. Examples of such compounds are: adenosine and its derivatives and retinol and its derivatives such as retinol palmitate, ascorbic acid and its derivatives such as magnesium ascorbyl phosphate and ascorbyl glucoside; nicotinic acid and its precursors such as nicotinamide; ubiquinone; glutathione and precursors thereof such as L-2-oxothiazolidine-4-carboxylic acid, the compounds C-glycosides and their derivatives as described in particular in EP-1345919, in particular C-beta-D-xylopyranoside-2-hydroxy-propane as described in particular in EP-1345919, plant extracts including sea fennel and extracts of olive leaves, as well as plant and hydrolysates thereof such as rice protein hydrolysates or soybean proteins; algal extracts and in particular laminaria, bacterial extracts, the sapogenins such as diosgenin and extracts of Dioscorea plants, in particular wild yam, comprising: the a-hydroxy acids, f3-hydroxy acids, such as salicylic acid and n-octanoyl-5-salicylic oligopeptides and pseudodipeptides and acyl derivatives thereof, in particular acid {2-[acetyl-(3-trifluoromethyl-phenyl)-amino]-3-methyl-}acetic acid and lipopeptides marketed by the company under the trade names SEDERMA Matrixyl 500 and Matrixyl 3000; lycopene, manganese salts and magnesium salts, especially gluconates, and mixtures thereof. In one embodiment, the cosmetic composition includes adenosine derivatives, such as non-phosphate derivatives of adenosine, such as in particular the 2'-deoxyadenosine, 2',3'-adenosine isopropoylidene; the toyocamycine, 1-methyladenosine, N-6-methyladenosine; adenosine N-oxide, 6-methylmercaptopurine riboside, and the 6-chloropurine riboside. Other derivatives include adenosine receptor agonists such as adenosine adenosine phenylisopropyl ("PIA"), 1-methylisoguanosine, N6-cyclohexyladenosine (CHA), N6-cyclopentyladenosine (CPA), 2-chloro-N6-cyclopentyladenosine, 2-chloroadenosine, N6-phenyladenosine, 2-phenylaminoadenosine, MECA, N 6-phenethyladenosine, 2-p-(2-carboxyethyl) phenethyl-amino-5'-N-ethylcarboxamido adenosine (CGS-21680), N-ethylcarboxamido-adenosine (NECA), the 5'(N-cyclopropyl)-carboxamidoadenosine, DPMA (PD 129.944) and metrifudil.

In one embodiment, the cosmetic composition includes a skin active agent that addresses oily skin. These agents can be sebo-regulating or antiseborrhoeic agents capable of regulating the activity of sebaceous glands. Exemplary skin active agents for addressing oily skin include: retinoic acid, benzoyl peroxide, sulfur, vitamin B6 (pyridoxine or) chloride, selenium, samphire—the cinnamon extract blends, tea and octanoylglycine such as—15 Sepicontrol A5 TEA from Seppic—the mixture of cinnamon, sarcosine and octanoylglycine marketed especially by Seppic under the trade name Sepicontrol AS—zinc salts such as zinc gluconate, zinc pyrrolidonecarboxylate (or zinc pidolate), zinc lactate, zinc aspartate, zinc carboxylate, zinc salicylate 20, zinc cysteate;—derivatives particularly copper and copper pidolate as Cuivridone Solabia—extracts from plants of *Arnica montana, Cinchona succirubra, Eugenia caryophyllata, Humulus lupulus, Hypericum perforatum, Mentha pipenta* 25 *Rosmarinus officinalis, Salvia officinalis* and *Thymus vulgaris*, all marketed for example by Maruzen—extracts of meadowsweet (*Spiraea ulmaria*), such as that sold under the name Sebonormine by Silab—extracts of the alga *Laminaria saccharina*, such as that sold under the 30 name Phlorogine by Biotechmarine—the root extracts of burnet mixtures (*Sanguisorba officinalis/Poterium officinale*), rhizomes of ginger (*Zingiber officinalis*) and cinnamon bark (*Cinnamomum cassia*), such as that sold under the name Sebustop by Solabia—extracts of flaxseed such as that sold under the name Linumine by Lucas Meyer—Phellodendron extracts such as those sold under the name Phellodendron extract BG by Maruzen or Oubaku liquid B by Ichimaru Pharcos—of argan oil mixtures extract of *Serenoa serrulata* (saw palmetto) extract and sesame seeds such as that sold under the name Regu SEB by Pentapharm—mixtures of extracts of willowherb, of *Terminalia chebula, nasturtium* and of bioavailable zinc (microalgae), such as that sold under the name Seborilys Green Tech;—extracts of *Pygeum afrianum* such as that sold under the name *Pygeum afrianum* sterolic lipid extract by Euromed—extracts of *Serenoa serrulata* such as those sold under the name Viapure Sabal by Actives International, and those sold by the company Euromed—of extracts of plantain blends, *Berberis aquifolium* and sodium salicylate 20 such as that sold under the name Seboclear Rahn—extract of clove as that sold under the name Clove extract powder by Maruzen—argan oil such as that sold under the name Lipofructyl Laboratories Serobiologiques; 25—lactic protein filtrates, such as that sold under the name Normaseb by Sederma—the seaweed *laminaria* extracts, such as that sold under the name Laminarghane by Biotechmarine—oligosaccharides seaweed *Laminaria digitata*, such as that sold under the name Phycosaccharide 30 AC by the company Codif—extracts of sugar cane such as that sold under the name Policosanol by the company Sabinsa, the sulfonated shale oil, such as that sold under the name Ichtyol Pale by Ichthyol—extracts of meadowsweet (*Spiraea ulmaria*) such as that sold under the name Cytobiol Ulmaire by societeLibiol—sebacic acid, especially sold in the form of a sodium polyacrylate gel under the name Sebosoft by Sederma—glucomannans extracted from konjac tuber and modified with alkylsulfonate chains such as that sold under the name Biopol Beta by Arch Chemical—extracts of *Sophora angustifolia*, such as those sold under the name *Sophora* powder or *Sophora* extract by Bioland—extracts of *Cinchona* bark *succirubra* such as that sold under the name Red Bark HS by Alban Muller—extracts of *Quillaja saponaria* such as that sold under the name 15 Panama wood HS by Alban Muller—glycine grafted onto an undecylenic chain, such as that sold under the name Lipacide UG OR by SEPPIC—the mixture of oleanolic acid and nordihydroguaiaretic acid, such as that sold under the form of a gel under the name AC.Net by Sederma; 20—phthalimidoperoxyhexanoic acid—citrate tri (C12-C13) sold under the name COSMACOL® ECI by Sasol; trialkyl citrate (C14-C15) sold under the name COSMACOL® ECL by Sasol—10-hydroxydecanoic acid, including mixtures acid-hydroxydecanoic October 25, sebacic acid and 1,10-decandiol such as that sold under the name Acnacidol BG by Vincience and mixtures thereof.

In some instances, the cosmetic composition may include a plurality of skin active agents such as phytosphingosine, cholesterol, sodium hyaluronate, and optionally an additional skin active agent. According to one embodiment, however, the cosmetic composition may include skin active agents chosen from phytosphingosine, cholesterol, sodium hyaluronate and a mixture thereof.

The skin active agents may be included in the cosmetic composition in an amount ranging from greater than zero to about to about 10 wt. %, based on the total weight of the composition. For example, the total amount of skin active agents may be from greater than zero to about 9 wt. %, greater than zero to about 8 wt. %, greater than zero to about 7 wt. %, greater than zero to about 6 wt. %, greater than zero to about 5 wt. %, greater than zero to about 4 wt. %, greater than zero to about 3 wt. %, greater than zero to about 2 wt. %, from about 10 ppm to about 10 wt. % (100,000 ppm), about 10 ppm to about 5 wt. % (50,000 ppm), about 10 ppm to about 2.5 wt. % (25,000 ppm), about 10 ppm to about 1 wt. % (10,000 ppm), about 10 ppm to about 0.5 wt. % (5,000 ppm), about 10 ppm to about 0.3 wt. % (3,000 ppm), about 10 ppm to about 0.2 wt. % (2,000 ppm), about 10 ppm to about 0.1 wt. % (1,000 ppm), or about 10 ppm to 500 ppm. Additionally or alternatively, the cosmetic composition may include an amount of skin active agents may be from greater than zero to 9 wt. %, greater than zero to 8 wt. %, greater than zero to 7 wt. %, greater than zero to 6 wt. %, greater than zero to 5 wt. %, greater than zero to 4 wt. %, greater than zero to 3 wt. %, greater than zero to 2 wt. %, from 10 ppm to 10 wt. % (100,000 ppm), 10 ppm to 5 wt. % (50,000 ppm), 10 ppm to 2.5 wt. % (25,000 ppm), 10 ppm to 1 wt. % (10,000 ppm), 10 ppm to 0.5 wt. % (5,000 ppm), 10 ppm to 0.3 wt. % (3,000 ppm), 10 ppm to 0.2 wt. % (2,000 ppm), 10 ppm to 0.1 wt. % (1,000 ppm), or 10 ppm to 500 ppm.

In some instances, the one or more skin active agents is present in an amount from 10, 20, 30, 40, 50, 60, 70, 80, 90, 100, 150, or 200 ppm to 500, 600, 700, 800, 900, 0.1 wt. % (1000 ppm), 0.5 wt. % (5,000 ppm), 1 wt. % (10,000 ppm), 5 wt. % (50,000 ppm), or 10 wt. % (100,000 ppm), including ranges and sub-ranges therebetween, based on the total weight of the cosmetic composition. For example, in one embodiment, the total amount of skin active agents ranges from 0.1 to 0.3% or about 0.1 to about 0.3 wt. %, based on the total weight of the cosmetic composition.

Silicone Oils

The cosmetic compositions described herein may comprise one or more silicone oils. Non-limiting examples of silicone oils include dimethicone, cyclomethicone, polysilicone-11, phenyl trimethicone, trimethylsilylamodimethicone, and stearoxytrimethylsilane. In some cases, the cosmetic composition includes dimethicone, and optionally additional oils, including additional silicone oils. Typically, the one or more silicone oils is a non-volatile silicon oil. In some embodiments, the silicone oil is polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl (methyldiphenyl)trisiloxanes or (2-phenylethyl)trimethylsiloxysilicates.

Other examples of silicone oils that may be mentioned include volatile linear or cyclic silicone oils, especially those with a viscosity 8 centistokes (8×106 m2/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

The amount of the one or more silicone oils in the composition may vary from, e.g., about 0.1 to about 25 wt. %, based on the total weight of the composition. For example, the total amount of silicone oils may range from about 0.1 to about 25 wt. %, about 0.1 to about 20 wt. %, from about 0.1 to about 15 wt. %, about 0.1 to about 10 wt. %, about 0.1 to about 8 wt. %, about 0.1 to about 6 wt. %, from about 0.5 to about 25 wt. % about 0.5 to about 20 wt. %, about 0.5 to about 15 wt. %, about 0.5 to about 10 wt. %, about 0.5 to about 8 wt. %, about 0.5 to 6 wt. %, or about 0.5 to 5 wt. %, from about 1 to about 25 wt. %, about 1 to about 20 wt. %, about 1 to about 15 wt. %, about 1 to about 10 wt. %, about 1 to about 8 wt. %, about 1 to about 6 wt. %, or about 1 to 5 wt. %, from about 1.5 to about 25 wt. %, about 1.5 to about 20 wt. %, about 1.5 to about 15 wt. %, about 1.5 to about 10 wt. %, about 1.5 to about 8 wt. %, about 1.5 to about 6 wt. %, or about 1.5 to 5 wt. %, from about 2 to about 25 wt. %, about 2 to about 20 wt. %, about 2 to about 15 wt. %, about 2 to about 10 wt. %, about 2 to about 8 wt. %, about 2 to about 6 wt. %, or about 2 to 5 wt. %, from about 2.5 to about 25 wt. %, about 2.5 to about 20 wt. %, about 2.5 to about 15 wt. %, about 2.5 to about 10 wt. %, about 2.5 to about 8 wt. %, about 2.5 to about 6 wt. %, or about 2.5 to 5 wt. %, from about 3 to about 25 wt. %, about 3 to about 20 wt. %, about 3 to about 15 wt. %, about 3 to about 10 wt. %, about 3 to about 8 wt. %, about 3 to about 6 wt. %, or about 3 to 5 wt. %, including ranges and sub-ranges therebetween, based on the total weight of the composition.

Additionally or alternatively, the total amount of silicone oils may be from 0.1 to 25 wt. %, 0.1 to 20 wt. %, from 0.1 to 15 wt. %, 0.1 to 10 wt. %, 0.1 to 8 wt. %, 0.1 to 6 wt. %, from 0.5 to 25 wt. %, 0.5 to 20 wt. %, 0.5 to 15 wt. %, 0.5 to 10 wt. %, 0.5 to 8 wt. %, 0.5 to 6 wt. %, or 0.5 to 5 wt. %, from 1 to 25 wt. %, 1 to 20 wt. %, 1 to 15 wt. %, 1 to 10 wt. %, 1 to 8 wt. %, 1 to 6 wt. %, or 1 to 5 wt. %, from 1.5 to 25 wt. %, 1.5 to 20 wt. %, 1.5 to 15 wt. %, 1.5 to 10 wt. %, 1.5 to 8 wt. %, 1.5 to 6 wt. %, or 1.5 to 5 wt. %, from 2 to 25 wt. %, 2 to 20 wt. %, 2 to 15 wt. %, 2 to 10 wt. %, 2 to 8 wt. %, 2 to 6 wt. %, or 2 to 5 wt. %, from 2.5 to 25 wt. %, 2.5 to 20 wt. %, 2.5 to 15 wt. %, 2.5 to 10 wt. %, 2.5 to 8 wt. %, 2.5 to 6 wt. %, or 2.5 to 5 wt. %, from 3 to 25 wt. %, 3 to 20 wt. %, 3 to 15 wt. %, 3 to 10 wt. %, 3 to 8 wt. %, 3 to 6 wt. %, or 3 to 5 wt. %, including ranges and sub-ranges therebetween, based on the total weight of the composition.

Preservatives

One or more preservatives may be included in the cosmetic compositions described herein. Suitable preservatives may include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, ethylenediamine-tetraacetic acid (EDTA), disodium EDTA, potassium sorbate, and/or grapefruit seed extract, or combinations thereof. More than one preservative may be included in the composition. Other preservatives are known in the cosmetics industries and include salicylic acid, DMDM Hydantoin, Formaldehyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, and Vitamin E (tocopherol). In one instance, the cosmetic composition has a plurality of preservatives including or chosen from disodium EDTA, phenoxyethanol, ethylhexylglycerin, tocopheryl acetate, and/or a mixture thereof.

The preservative is optionally included in an amount ranging from about 0.01 wt. % to about 5 wt. %, about 0.15% to about 1 wt. %, or about 1 wt. % to about 3 wt. %, based on the total weight of the composition.

pH Adjuster

The cosmetic composition may include one or more pH adjusters to increase or decrease the overall pH of the cosmetic composition. For example, one or more acids may be included to decrease the pH of the cosmetic composition. Examples of suitable acids for decreasing the pH of the cosmetic composition include, but are not limited to, citric acid, acetic acid, and the like. The cosmetic composition may include one or more bases, such as sodium hydroxide, potassium hydroxide and the like, to decrease the pH of the cosmetic composition. Additional or alternative acids and bases that are suitable for adjusting the pH of the cosmetic composition are readily known to one of ordinary skill in the art.

The cosmetic composition may, desirably, have a pH of pH of about 4 to about 7, preferably about 4.5 to about 6.5 or about 5.5 to about 6.5. Additionally or alternatively, the pH of the cosmetic composition may range from 4 to 7, preferably from 4.5 to 6.5, or preferably from 5.5 to 6.5. In one instance, the pH of the cosmetic composition is 6 or about 6.

The amount of the pH adjuster in the cosmetic composition may be based on the desired pH of the final cosmetic composition and/or product. For example, the total amount of the pH adjuster may range from about 0.05 to about 20 wt. %, based on the total weight of the composition. In some instances, the total amount of pH adjuster is from about 0.05 to about 15 wt. %, about 0.5 to about 10 wt. %, about 1 to about 5 wt. %, about 1.5 to about 4 wt. %, or about 2.0 to about 3 wt. %, including ranges and sub-ranges therebetween, based on the total weight of the composition. Additionally or alternatively, the cosmetic compositions may include an amount of pH adjuster ranging from 0.05 to 15 wt. %, 0.5 to 10 wt. %, 1 to 5 wt. %, 1.5 to 4 wt. %, or 2.0 to 3 wt. %, including ranges and sub-ranges therebetween, based on the total weight of the composition.

Water

The total amount of water in the cosmetic composition can vary, but is typically about 30 to about 95 wt. %, based on the total weight of the cleansing composition. In some instances, total amount of water is about 30 to about 90 wt. %, about 30 to about 85 wt. %, about 30 to about 80 wt. %, about 35 to about 90 wt. %, about 35 to about 85 wt. %, about 35 to about 80 wt. %, about 40 to about 90 wt. %, about 40 to about 85 wt. %, about 40 to about 80 wt. %, about 45 to about 90 wt. %, about 45 to about 85 wt. %, about 45 to about 80 wt. %, about 50 to about 90 wt. %, about 50 to about 85 wt. %, about 50 to about 80 wt. %, about 55 to about 90 wt. %, about 55 to about 85 wt. %, about 55 to about 80 wt. %, about 60 to about 90 wt. %, about 60 to about 85 wt. %, about 60 to about 80 wt. %, about 65 to about 90 wt. %, about 65 to about 85 wt. %, or about 65 to about 80 wt. %, based on the total weight of the cleansing composition.

In some instances, the cosmetic compositions may be free or essentially free of propylene glycol and/or ethoxydiglycol.

The cosmetic compositions of the instant disclosure are preferably stable. The term "stable" as used herein means that the cosmetic composition does not visually phase separate and produces a pressure within a closed container after four weeks at a temperature of 45° C. of 0.5 bar or less. In some instances, the cosmetic composition does not visually phase separate and produces a pressure within a closed container after four weeks at a temperature of 45° C. of 0.4 bar or less, 0.3 bar or less, 0.25 bar or less, 0.2 bar or less, 0.15 bar or less or 0.1 bar or less.

The instant disclosure also relates to methods or processes for making/manufacturing the cosmetic compositions described herein. It also encompasses the products prepared by these methods or processes. Typically, a process for making the cosmetic compositions of the instant disclosure comprises the formation of an oil phase and the formation of a separate aqueous phase (containing water), both phases are heated and combined while warm. Each phase may be heated to the same temperature or may be heated to different temperatures.

The thickening agents may be added to the aqueous phase of the cosmetic compositions. In some instances, however, the one or more emulsifiers and/or the thicken agents are added to the oil phase. Additionally or alternatively, thickening agents may be added post-emulsification—for instance, ammonium polyacryloydldimethyl taurate may be added post-emulsification.

After combining the oil phase and the aqueous phase to form an emulsion, the composition is typically allowed to cool. Additional components may be added during the time of emulsification or after. For example, certain fragrances, colorings, exfoliants, active ingredients, etc., may be added to the aqueous phase, the fatty phase, or after emulsification.

The instant disclosure also relates to methods of using the cosmetic compositions described herein. For example, the cosmetic compositions can be used in a method that comprises applying the cosmetic compositions to this skin of humans. In some cases, the composition is applied to the face. Furthermore, the cosmetic composition can be used in methods for treating dryness of the skin, repairing damage to skin (for example, damage from photoaging), and for diminishing the appearance of wrinkles, dark spots, and uneven skin texture of skin. The aforementioned methods are non-therapeutic.

The cosmetic composition may be applied once per day, twice per day, or more than once or twice per day. In some cases, the composition is applied in the evenings before bed. In other cases, the compositions are applies in the morning. In still other cases, the composition may be applied immediately after washing the skin. The compositions may be used once, or for a series of days, weeks, or months. For example, the compositions may be used daily for a period of 1, 2, 3, 4, 5, 6, 7, 8 or more weeks, or months.

Embodiments

In certain embodiments, the cosmetic compositions of the instant disclosure optionally form an oil-in-water emulsion, the cosmetic compositions:
- about 5 to about 15 wt. %, preferably about 7 to about 13 wt. %, more preferably about 9 to about 11 wt. % of ascorbic acid, such as L-ascorbic acid;
- one or more ceramides in an amount preferably ranging from greater than zero to about 4 wt. %, more preferably about 50 ppm to about 3 wt. %, the one or more ceramides chosen from ceramide-EOS, ceramide-NS, ceramide-NP, ceramide-EOH, ceramide-AS, ceramide-NH, ceramide-AP, ceramide-AH, Ceramide-OS, ceramide-OH, and a mixture thereof;
- about 0.1 to about 10 wt. %, preferably about 0.3 to about 7 wt. %, more preferably about 0.5 to about 5 wt. % of panthenol;
- about 1 to about 20 wt. %, preferably about 1.5 to about 13 wt. %, more preferably about 2 to about 9 wt. % of one or more monoalcohols having from 2 to 6 carbon atoms, such as those chosen from ethanol, propanol, butanol, pentanol, hexanol, isopropyl alcohol, cycohexanol, isobutyl alcohol, 2-methyl-2-butanol (2-methylbutan-2-ol), and a mixture thereof;
- about 1 to about 25 wt. %, preferably about 2 to about 17 wt. %, more preferably about 3 to about 10 wt. % of one or more polyols, including, for example, polyols having from 2 to 15 carbon atoms and at least two hydroxyl groups, such as those chosen from glycol, butylene glycol, hexylene glycol, pentylene glycol, 1,3-propanediol, diethylene glycol, dipropylene glycol, caprylyl glycol, glycerin, and a mixture thereof;
- about 1 to about 25 wt. %, preferably about 2 to about 17 wt. %, more preferably about 3 to about 10 wt. % of one or more fatty compounds, such as those chosen from fatty acid monoesters and diesters, polyol esters, polyglycerol esters, polyglycerol polyricinoleate, polyglycerol poly-12-hydroxystearate, polyglycerol dimerate isostearate, ethylhexanoate, polyglycerol esters, and a mixture thereof;
- one or more emulsifiers in an amount preferably ranging from greater than zero to about 4 wt. %, more preferably about 50 ppm to about 3 wt. %, more preferably about 80 ppm to 2 wt. %, the one or more emulsifiers preferably being nonionic emulsifier, such as, e.g., sodium lauroyl lactylate;
- optionally, one or more cationic surfactants in an amount preferably ranging from greater than zero to about 5 wt. %, more preferably about 50 ppm to about 3 wt. %, more preferably about 100 ppm to about 2 wt. %, the one or more cationic surfactants being preferably chosen from quaternary ammonium compounds, such as, e.g., behentrimonium methosulfate; and
- water in an amount quantum satis to 100 wt. %, preferably about 40 to about 90 wt. %, more preferably about 45 to about 85 wt %, more preferably about 50 to about 80 wt %;

wherein the weight percentages are based on the total weight of the cosmetic composition and the cosmetic composition has a viscosity of about 5,000 to about 50,000 cP, preferably about 7,000 to about 45,000 cP, more preferably about 9,000 to about 40,000 cP at 25° C.

In other embodiments, the cosmetic compositions of the instant disclosure optionally form an oil-in-water emulsion that produces a pressure within a closed container that does not increase by 1 bar or more, preferably 0.5 bar or more, more preferably 0.4 bar or more after four weeks at a temperature of 45° C., the cosmetic compositions comprising:
- about 7 to about 13 wt. %, preferably about 9 to about 11 wt. %, more preferably about 10.% of ascorbic acid, such as L-ascorbic acid;
- one or more ceramides in an amount preferably ranging from 50 ppm to about 2 wt. %, more preferably about 80 ppm to about 1 wt. %, the one or more ceramides chosen from ceramide-EOS, ceramide-NS, ceramide-NP, ceramide-EOH, ceramide-AS, ceramide-NH, ceramide-AP, ceramide-AH, Ceramide-OS, ceramide-OH, and a mixture thereof;
- about 0.3 to about 7 wt. %, preferably about 0.5 to about 5 wt. %, more preferably about 0.7 to about 2 wt. % of panthenol;
- about 1 to about 13 wt. %, preferably about 1.5 to about 9 wt. %, more preferably about 2 to about 7 wt. % of one or more monoalcohols having from 2 to 6 carbon atoms, such as those chosen from ethanol, propanol, butanol, pentanol, hexanol, isopropyl alcohol, cycohexanol, isobutyl alcohol, 2-methyl-2-butanol (2-methylbutan-2-ol), and a mixture thereof, the one or more monoalcohols preferably being ethanol;
- about 2 to about 17 wt. %, preferably about 3 to about 10 wt. %, more preferably about 3.5 to about 7 wt. % of one or more polyols, including, for example, polyols having from 2 to 15 carbon atoms and at least two hydroxyl groups, such as those chosen from glycol, butylene glycol, hexylene glycol, pentylene glycol, 1,3-propanediol, diethylene glycol, dipropylene glycol, caprylyl glycol, glycerin, and a mixture thereof, the one or more polyols preferably including glycerin;
- about 2 to about 17 wt. %, preferably about 3 to about 10 wt. %, more preferably about 3.5 to about 6 wt. % of one or more fatty compounds, such as those chosen from fatty acid monoesters and diesters, polyol esters, polyglycerol esters, polyglycerol polyricinoleate, polyglycerol poly-12-hydroxystearate, polyglycerol dimerate isostearate, ethylhexanoate, polyglycerol esters, and a mixture thereof, the one or more fatty compounds preferably including one or more fatty acid monoesters;
- one or more emulsifiers in an amount preferably ranging from greater than zero to about 3 wt. %, more preferably about 50 ppm to about 2 wt. %, more preferably about 80 ppm to 1 wt. %, the one or more emulsifiers preferably being a nonionic emulsifier, such as, e.g., sodium lauroyl lactylate;
- optionally, one or more cationic surfactants in an amount preferably ranging from greater than zero to about 4 wt. %, more preferably about 50 ppm to about 2 wt. %, more preferably about 100 ppm to about 1 wt. %, the one or more cationic surfactants being preferably chosen from quaternary ammonium compounds, such as, e.g., behentrimonium methosulfate; and water in an amount quantum satis to 100 wt. %, preferably about 50 to about 85 wt. %, more preferably about 55 to about 80 wt %, more preferably about 60 to about 75 wt %;

wherein the weight percentages are based on the total weight of the cosmetic composition and the cosmetic composition has a viscosity of about 5,000 to about 50,000 cP, preferably about 7,000 to about 45,000 cP, more preferably about 9,000 to about 40,000 cP at 25° C.

The embodiments of the cosmetic compositions may optionally include about 1 to about 20 wt. %, preferably about 1.5 to about 5 wt. %, of one or more thickening agents. In at least one embodiment, the cosmetic composition includes greater than zero to about 5 wt. %, preferably about 100 ppm to about 5 wt. %, more preferably about 0.1 to about 4 wt. % of one or more skin active agent, such as those chosen from phytosphingosine, cholesterol, sodium hyaluronate, and a mixture thereof. In some embodiments, the cosmetic composition is free of propylene glycol and/or ethoxydiglycol.

In certain embodiments, a product containing a cosmetic composition comprises a container, such as an aerosol can; and a cosmetic composition in accordance with one or more of any of the embodiments discussed herein, the cosmetic composition being contained within the container, wherein a pressure within the container does not increase by increase by 1 bar or more, preferably 0.5 bar or more, more preferably 0.4 bar or more after four weeks at a temperature of 45° C.

EXAMPLES

Implementation of the present disclosure is provided by way of the following examples. The following examples serve to elucidate aspects of the technology without being limiting in nature.

Example 1

Inventive Compositions

TABLE 1

| | | INCI US | A | B | C |
|---|---|---|---|---|---|
| (a) | Ascorbic Acid | ASCORBIC ACID | 10 | 10 | 10 |
| (b) | Ceramides | CERAMIDE EOP, CERAMIDE NP, AND CERAMIDE AP | ≤1 | ≤1 | ≤1 |
| (c) | Pantothenic acid | PANTHENOL | 1 | 1 | 1 |
| (d) | Monoalcohol | ETHANOL | 3 | 3 | 3 |
| (e) | Polyols | CAPRYLYL GLYCOL and GLYCERIN | 4.5 | 4.5 | 4.5 |

TABLE 1-continued

| | | INCI US | A | B | C |
|---|---|---|---|---|---|
| (f) | Fatty Compounds | CETEARYL ALCOHOL, CETEARYL ETHYLHEXANOATE, and ISOPROPYL MYRISTATE | 4.8 | 4.1 | 4.1 |
| (g) | Emulsifier | SODIUM LAUROYL LACTYLATE | 0.1 | 0.01 | 0.01 |
| (h) | Cationic Surfactant | BEHENTRIMONIUM METHOSULFATE | 0.3 | 0.03 | |
| (j) | Thickening Agents | AMMONIUM POLYACRYLOYL-DIMETHYL TAURATE, XANTHAN GUM, AND/OR CARBOMER | 1.6 | 1.6 | 1.6 |
| (k) | Skin Active Agents | PHYTOSPHINGOSINE, CHOLESTEROL, and/or SODIUM HYALURONATE | 0.2 | 0.2 | 0.2 |
| (l) | Silicone Preservatives | DIMETHICONE | 4 | 4 | 4 |
| | | DISODIUM EDTA, PHENOXYETHANOL, AND/OR ETHYLHEXYL-GLYCERIN | ≤2 | ≤2 | ≤2 |
| | | TOCOPHERYL ACETATE | | 0.5 | 0.5 |
| | pH Adjuster | SODIUM HYDROXIDE | 2.3 | 2.3 | 2.3 |
| (i) | Water | WATER | QS 100 | QS 100 | QS 100 |

Example 2

Inventive Compositions A, B, C of Example 1 and several comparative compositions were tested for stability. Stability was assessed by measuring the amount of pressure the composition produced over time in a closed container. Degradation of ascorbic acid produces carbon dioxide, which creates pressure inside a closed container. Therefore, higher pressure represents less stability of the ascorbic acid.

Comparative Composition D was prepared by adding the same amount of ceramides and the same amount of behentrimonium methosulfate as contained in Inventive Composition A to a first commercial benchmark product containing 10 wt. % of ascorbic acid. The commercial benchmark product did not already include ceramides.

Comparative Composition E was prepared by adding the same amount of ceramides and the same amount of behentrimonium methosulfate as contained in Inventive Composition B to the same first commercial benchmark product used as the base for Comparative Composition D.

Comparative Composition F represents the first commercial benchmark product used for Comparative Compositions D and E, but ceramides and behentrimonium methosulfate were not added into Comparative Composition F.

Comparative Composition G represents a second commercial benchmark product containing 10 wt. % of ascorbic acid. It does not include ceramides and behentrimonium methosulfate, and ceramides and behentrimonium methosulfate were not added into Comparative Composition G.

The stability of the compositions was assessed by measuring the amount of pressure produced within a closed container over time. Degradation of ascorbic acid produces carbon dioxide, which creates pressure inside a closed container. Therefore, higher pressure represents less stability of the ascorbic acid. Each of the foregoing compositions was stored in a separate aluminum aerosol can (without a spray actuator) and maintained at a constant temperature of 45° C., for four weeks. A manometer was coupled to the aluminum aerosol cans and used to measure the pressure (in bar) on a weekly basis. The results are presented in the table below.

TABLE 2

|         | A    | B    | C    | D    | E    | F    | G    |
|---------|------|------|------|------|------|------|------|
| 1 week  | 0.23 | 0.18 | 0.18 | 0.51 | 0.33 | 0.22 | 0.35 |
| 2 weeks | 0.22 | 0.25 | 0.22 | 0.68 | 0.51 | 0.24 | 0.55 |
| 3 weeks | 0.35 | 0.28 | 0.29 | 0.96 | 0.61 | 0.32 | 0.58 |
| 4 weeks | 0.37 | 0.38 | 0.3  | 1.2  | 0.78 | 0.35 | 0.75 |

As shown above, Inventive Compositions A, B, and C exhibited very little increase in pressure indicating that the ascorbic acid was stabilized and remained stable over time. Comparative compositions D and E, to which ceramides and behentrimonium methosulfate were added in order to produce compositions similar to the inventive compositions A and B (which contain high amounts of ascorbic acid and ceramides) produced more than double the pressure than the inventive compositions, indicating that the ascorbic acid was far less stable. Comparative Composition F had similar pressure results as Inventive Compositions A, B, and C, but Comparative Composition F did not include ceramides and behentrimonium methosulfate. When ceramides and behentrimonium methosulfate were added to Comparative Composition F, resulting in Comparative Compositions D and E, the stability greatly deteriorated. Comparative Composition G, which represents a second commercial benchmark product that does not include ceramides and behentrimonium methosulfate exhibited high pressure, indicating that the ascorbic acid was not stabilized. The data show that the cosmetic compositions according to the instant disclosure, which include high amounts of ascorbic acid and ceramides are surprisingly stable.

The term "INCI" is an abbreviation of International Nomenclature of Cosmetic Ingredients, which is a system of names provided by the International Nomenclature Committee of the Personal Care Products Council to describe personal care ingredients.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

All components and elements positively set forth in this disclosure can be negatively excluded from the claims. In other words, the cosmetic compositions of the instant disclosure can be free or essentially free of all components and elements positively recited throughout the instant disclosure.

Some of the various categories of components identified may overlap. In such cases where overlap may exist and the composition includes both components (or the composition includes more than two components that overlap), an overlapping compound does not represent more than one component. For example, a fatty acid may be characterized as both a nonionic surfactant and a fatty compound. If a particular composition includes both a nonionic surfactant and a fatty compound, a single fatty acid will serve as only the nonionic surfactant or as only the fatty compound (the single fatty acid does not serve as both the nonionic surfactant and the fatty compound).

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

As used herein, the terms "comprising," "having," and "including" are used in their open, non-limiting sense.

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

The expression "one or more" means "at least one" and thus includes individual components as well as mixtures/combinations.

Other than in the operating examples, or where otherwise indicated, all numbers expressing quantities of ingredients and/or reaction conditions may be modified in all instances by the term "about," meaning within +/−5% of the indicated number.

The term "treat" (and its grammatical variations) as used herein refers to the application of the compositions of the present disclosure onto the surface of keratinous substrates such as skin, in particular, the skin of the head, face, and neck.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of alkoxylated compounds, for example, ethoxylated thickeners and/or ethoxylated surfactants. Likewise, a particular composition may be free or essentially free of sulfates, such as sulfate surfactants.

The invention claimed is:
1. A cosmetic composition comprising:
(a) about 5 to about 15 wt. % of ascorbic acid;
(b) one or more ceramides;
(c) about 0.1 to about 10 wt. % of panthenol;
(d) about 1 to about 20 wt. % of one or more monoalcohols having from 2 to 6 carbon atoms;
(e) about 1 to about 25 wt. % of one or more polyols;
(f) about 1 to about 25 wt. % of one or more fatty compounds;
(g) one or more emulsifiers;
(h) optionally, one or more cationic surfactants; and
(i) water;
wherein the weight percentages are based on the total weight of the cosmetic composition, the cosmetic composition has a viscosity of about 5,000 cP to 50,000 cP at 25° C., and a pressure produced by the cosmetic composition within a closed container does not increase by 0.5 bar or more after four weeks at a temperature of 45° C.

2. The cosmetic composition of claim 1, wherein the one or more ceramides are chosen from ceramide-EOS, ceramide-NS, ceramide-NP, ceramide-EOH, ceramide-AS, ceramide-NH, ceramide-AP, ceramide-AH, Ceramide-OS, ceramide-OH, and a mixture thereof.

3. The cosmetic composition of claim 1, wherein the total amount of ceramides is greater than zero to about 5 wt. %, based on the total weight of the composition.

4. The cosmetic composition of claim 1, wherein the one or more monoalcohols are chosen from ethanol, propanol, butanol, pentanol, hexanol, isopropyl alcohol, cycohexanol, isobutyl alcohol, 2-methyl-2-butanol (2-methylbutan-2-ol), and a mixture thereof.

5. The cosmetic composition of claim 1, wherein the one or more monoalcohols comprise ethanol.

6. The cosmetic composition of claim 1, wherein the one or more polyols are chosen from polyols having from 2 to 15 carbon atoms and at least two hydroxyl groups.

7. The cosmetic composition of claim 6, wherein the one or more polyols are chosen from ethylene glycol, butylene glycol, hexylene glycol, pentylene glycol, 1,3-propanediol, diethylene glycol, dipropylene glycol, caprylyl glycol, glycerin, and a mixture thereof.

8. The cosmetic composition of claim 7, wherein the one or more glycols comprise glycerin.

9. The cosmetic composition of claim 1, wherein the one or more fatty compounds comprise one or more alkyl esters chosen from fatty acid monoesters and diesters, polyol esters, polyglycerol esters, polyglycerol polyricinoleate, polyglycerol poly-12-hydroxystearate, polyglycerol dimerate isostearate, ethylhexanoate, polyglycerol esters, and a mixture thereof.

10. The cosmetic composition of claim 9, wherein the fatty compound comprises one or more fatty acid monoesters.

11. The cosmetic composition of claim 1, wherein the one or more emulsifiers comprise one or more nonionic emulsifiers.

12. The cosmetic composition of claim 1, wherein the amount of water is about 40 to about 90 wt. %, based on the total weight of the cosmetic composition.

13. The cosmetic composition of claim 1 comprising one or more cationic surfactants, wherein the one or more cationic surfactants are chosen from quaternary ammonium compounds.

14. The cosmetic composition of claim 13, wherein the total amount of cationic surfactants is greater than zero to about 5 wt. %, based on the total weight of the cosmetic composition.

15. The cosmetic composition of claim 1, further comprising:
(j) about 1 to about 20 wt. % of one or more thickening agents; and/or
(k) greater than zero to about 5 wt. % of one or more skin active agents.

16. The cosmetic composition of claim 1, wherein the cosmetic composition is in the form of an emulsion.

17. A cosmetic composition comprising:
(a) about 5 to about 15 wt. % of ascorbic acid;
(b) greater than zero to about 5 wt. % of one or more ceramides chosen from ceramide-EOS, ceramide-NS, ceramide-NP, ceramide-EOH, ceramide-AS, ceramide-NH, ceramide-AP, ceramide-AH, Ceramide-OS, ceramide-OH, and a mixture thereof;
(c) about 0.1 to about 10 wt. % of panthenol;
(d) about 1 to about 20 wt. % of one or more monoalcohols having from 2 to 6 carbon atoms;
(e) about 1 to about 25 wt. % of one or more glycols chosen from ethylene glycol, butylene glycol, hexylene glycol, pentylene glycol, 1,3-propanediol, diethylene glycol, dipropylene glycol, caprylyl glycol, glycerin, and a mixture thereof;
(f) about 1 to about 25 wt. % of one or more fatty compounds;
(g) one or more nonionic emulsifiers;
(h) optionally, greater than zero to about 5 wt. % of one or more cationic surfactants;
(i) about 40 to about 90 wt. % of water;
(j) about 1 to about 20 wt. % of one or more thickening agents; and
(k) greater than zero to about 5 wt. % of one or more skin active agents,
wherein the weight percentages are based on the total weight of the cosmetic composition, the cosmetic composition has a viscosity of about 5,000 cP to 50,000 cP at 25° C., and a pressure produced by the cosmetic composition within a closed container does not increase by 0.5 bar or more after four weeks at a temperature of 45° C.

18. A product comprising:
(i) a container; and
(ii) a cosmetic composition of claim 1 contained within the container,
wherein a pressure within the container does not increase by 0.5 bar or more after four weeks at a temperature of 45° C.

19. A method for treating skin comprising applying a cosmetic composition of claim 1 to the skin.

* * * * *